(12) United States Patent
Chen et al.

(10) Patent No.: US 7,585,669 B2
(45) Date of Patent: Sep. 8, 2009

(54) COMPOSITIONS AND METHODS FOR TREATING OR PREVENTING PNEUMOCOCCAL INFECTION

(75) Inventors: Michael C. Chen, Potomac, MD (US); Chuang-Jiun Chiou, Columbia, MD (US); Zhongming Li, Gaithersberg, MD (US); Dong-Sheng Chen, Potomac, MD (US)

(73) Assignee: Synergy America, Inc., Rockville, MD (US)

( * ) Notice: Subject to any disclaimer, the term of this patent is extended or adjusted under 35 U.S.C. 154(b) by 317 days.

(21) Appl. No.: 11/748,270

(22) Filed: May 14, 2007

(65) Prior Publication Data

US 2008/0199952 A1   Aug. 21, 2008

Related U.S. Application Data

(62) Division of application No. 10/702,305, filed on Nov. 6, 2003, now Pat. No. 7,217,791.

(60) Provisional application No. 60/424,497, filed on Nov. 7, 2002.

(51) Int. Cl.
*C12N 15/00* (2006.01)
(52) U.S. Cl. .................................. 435/320.1
(58) Field of Classification Search ............. None
See application file for complete search history.

(56) References Cited

U.S. PATENT DOCUMENTS 6,342,224 B1   1/2002   Bruck et al.

FOREIGN PATENT DOCUMENTS

| EP | 0 687 688 | 12/1995 |
| WO | WO90/06951 | 6/1990 |
| WO | WO99/03884 | 1/1999 |

OTHER PUBLICATIONS

McDaniel, et al., "Immunization with a Plasmid Expressing Pneumococcal Surface protein A (PspA) can Elicit Protection Against Fatal Infection with *Streptococcus pneumoniae*," Gene Therapy, 1997, vol. 4, No. 4, pp. 375-377.
EPO communication mailed Jul. 30, 2007.

*Primary Examiner*—Mark Navarro
(74) *Attorney, Agent, or Firm*—Occhiuti Rohlicek & Tsao LLP

(57) ABSTRACT

The invention provides polypeptides, polysaccharide-polypeptide conjugates, and expression vectors for treating or preventing pneumococcal infection. The compositions induce an anti-pneumococcal immune response when administered to a mammal. The compositions can be used prophylactically to vaccinate an individual and/or therapeutically to induce a therapeutic immune response in an infected individual.

18 Claims, 13 Drawing Sheets

US 7,585,669 B2

COMPOSITIONS AND METHODS FOR TREATING OR PREVENTING PNEUMOCOCCAL INFECTION

RELATED U.S. APPLICATION

This application is a divisional of U.S. patent application Ser. No. 10/702,305, now U.S. Pat. No. 7,217,791, filed Nov. 6, 2003, which claims priority from U.S. Provisional Patent Application No. 60/424,497, filed Nov. 7, 2002. The entire content of the prior applications is incorporated herein by reference.

FIELD OF THE INVENTION

The invention relates to polypeptides, pneumococcal polysaccharide-polypeptide conjugates, expression vectors encoding pneumococcal polypeptides, methods of inducing an anti-pneumococcal immune response, and methods of treating and preventing pneumococcal infection.

BACKGROUND OF THE INVENTION

*Streptococcus pneumoniae* (*S. pneumoniae*) is a common cause of bacterial pneumonia, meningitis, otitis media, and bacteremia in children, the elderly, and immunodeficient individuals. *S. pneumoniae* can be subdivided into approximately 90 serotypes, based on the capsular polysaccharide of the organism. However, disease is generally caused by approximately 30 types of *S. pneumoniae* isolates. The World Health Organization estimates that there are one million deaths among children due to pneumococcal meningitis and sepsis each year, with 98% of these deaths occurring in developing countries. The emergence of pneumococcal strains with antimicrobial resistance underscores the need for treating and preventing pneumococcal infection by methods in addition to antimicrobials.

SUMMARY OF THE INVENTION

In one aspect, the invention features a composition containing a polypeptide conjugated to a *S. pneumoniae* capsular polysaccharide, wherein the polypeptide contains a fragment of at least 400 contiguous amino acids of a *S. pneumoniae* pneumolysin protein, wherein the polypeptide lacks the amino acid sequence KVEND (SEQ ID NO:22) (e.g., at the carboxy terminus), wherein the polypeptide lacks hemolytic activity, and wherein the composition elicits an immune response (e.g., a humoral immune response and/or a cellular immune response) against *S. pneumoniae* when administered to a mammal. The immune response can be a prophylactic and/or therapeutic immune response.

The *S. pneumoniae* pneumolysin protein can have the amino acid sequence of SEQ ID NO:1. In some embodiments, the polypeptide contains amino acids 1-460 of SEQ ID NO:1. In other embodiments, the polypeptide contains amino acids 1-464 of SEQ ID NO:1, amino acids 1-465 of SEQ ID NO:1, amino acids 1-466 of SEQ ID NO:1, amino acids 1-469 of SEQ ID NO:1, or amino acids 1-470 of SEQ ID NO:1.

The polypeptide can optionally lack the amino acid sequence EDKVEND (SEQ ID NO:23) or the amino acid sequence YPQVEDKVEND (SEQ ID NO:24).

In some embodiments, the polypeptide consists of amino acid residues 1-460 of SEQ ID NO:1, amino acid residues 1-464 of SEQ ID NO:1, amino acid residues 1-465 of SEQ ID NO:1, amino acid residues 1-466 of SEQ ID NO:1, amino acid residues 1-469 of SEQ ID NO:1, or amino acid residues 1-470 of SEQ ID NO:1.

In some embodiments, the capsular polysaccharide is selected from the group consisting of serotype 4, 6B, 9V, 14, 18C, 19F, and 23F. In one example, the capsular polysaccharide is serotype 14. In another example, the capsular polysaccharide is serotype 18C. The composition can optionally contain a plurality of different capsular polysaccharides selected from the group consisting of serotype 4, 6B, 9V, 14, 18C, 19F, and 23F.

The immune response elicited by the composition can be directed against a *S. pneumoniae* capsular polysaccharide, against a *S. pneumoniae* pneumolysin protein, or against a *S. pneumoniae* capsular polysaccharide and a *S. pneumoniae* pneumolysin protein.

In another aspect, the invention features a mammalian expression vector containing a promoter operably linked to a nucleotide sequence containing a nucleic acid encoding a polypeptide containing a fragment of at least 400 contiguous amino acids of a *S. pneumoniae* pneumolysin protein, wherein the polypeptide lacks the amino acid sequence KVEND (SEQ ID NO:22) (e.g., at the carboxy terminus), wherein the polypeptide lacks hemolytic activity, and wherein the polypeptide elicits an immune response (e.g., a humoral immune response and/or a cellular immune response) against *S. pneumoniae* when the expression vector is administered to a mammal. The immune response can be a prophylactic and/or therapeutic immune response.

The *S. pneumoniae* pneumolysin protein can have the amino acid sequence of SEQ ID NO:1. In some embodiments, the encoded polypeptide contains amino acids 1-460 of SEQ ID NO:1. In other embodiments, the encoded polypeptide contains amino acids 1-464 of SEQ ID NO:1, amino acids 1-465 of SEQ ID NO:1, amino acids 1-466 of SEQ ID NO:1, amino acids 1-469 of SEQ ID NO:1, or amino acids 1-470 of SEQ ID NO:1.

The encoded polypeptide can optionally lack the amino acid sequence EDKVEND (SEQ ID NO:23) or the amino acid sequence YPQVEDKVEND (SEQ ID NO:24).

In some embodiments, the encoded polypeptide consists of amino acid residues 1-460 of SEQ ID NO:1, amino acid residues 1-464 of SEQ ID NO:1, amino acid residues 1-465 of SEQ ID NO:1, amino acid residues 1-466 of SEQ ID NO:1, amino acid residues 1-469 of SEQ ID NO:1, or amino acid residues 1-470 of SEQ ID NO:1.

The immune response elicited by the encoded polypeptide can be directed against a *S. pneumoniae* pneumolysin protein.

In another aspect, the invention features a mammalian expression vector containing a promoter operably linked to a nucleotide sequence containing a nucleic acid encoding a *S. pneumoniae* autolysin polypeptide, wherein the polypeptide elicits an immune response (e.g., a humoral immune response and/or a cellular immune response) against *S. pneumoniae* when the expression vector is administered to a mammal. The immune response can be a prophylactic and/or therapeutic immune response.

In some embodiments, the encoded polypeptide contains the amino acid sequence of SEQ ID NO:14. In other embodiments, the encoded polypeptide consists of the amino acid sequence of SEQ ID NO:14.

In another aspect, the invention features a mammalian expression vector containing a promoter operably linked to a nucleotide sequence containing a nucleic acid encoding a *S. pneumoniae* pneumococcal surface protein A polypeptide, wherein the polypeptide elicits an immune response (e.g., a humoral immune response and/or a cellular immune response) against *S. pneumoniae* when the expression vector is administered to a mammal. The immune response can be a prophylactic and/or therapeutic immune response.

In some embodiments, the encoded polypeptide contains the amino acid sequence of SEQ ID NO:18. In other embodiments, the encoded polypeptide consists of the amino acid sequence of SEQ ID NO:18.

In another aspect, the invention features a polypeptide consisting of an amino acid sequence selected from the group consisting of amino acids 1-460 of SEQ ID NO:1, amino acids 1-464 of SEQ ID NO:1, amino acids 1-466 of SEQ ID NO:1, and amino acids 1-469 of SEQ ID NO:1.

In another aspect, the invention features a method of inducing an immune response in a mammal by administering to a mammal an amount of a composition described herein that is effective to induce an immune response against *S. pneumoniae* in the mammal. The immune response can be a prophylactic and/or therapeutic immune response.

In some embodiments, the immune response is cross-reactive against at least one *Streptococcus pneumoniae* serotype that differs from the serotype of the capsular polysaccharide (e.g., serotype 7, 6B, 18C, or 23F) present in the composition. In some embodiments, the immune response is cross-reactive against at least one non-*Streptococcus pneumoniae* member of the *Streptococcus* genus.

In another aspect, the invention features a method of inducing an immune response in a mammal by administering to a mammal an amount of an expression vector described herein (e.g., a pneumolysin, pseudopneumolysin, autolysin, or pneumococcal surface protein A expression vector) that is effective to induce an immune response against *S. pneumoniae* in the mammal. The immune response can be a prophylactic and/or therapeutic immune response. In some embodiments, the immune response is cross-reactive against at least one non-*Streptococcus pneumoniae* member of the *Streptococcus* genus.

In another aspect, the invention features a method of inducing an immune response in a mammal by: administering to a mammal a mammalian expression vector containing a promoter operably linked to a nucleotide sequence containing a nucleic acid encoding a *Streptococcus pneumoniae* pneumolysin polypeptide or antigenic fragment thereof; and administering to the mammal a purified *S. pneumoniae* pneumolysin polypeptide or antigenic fragment thereof, wherein the combined administrations elicit an immune response against *S. pneumoniae* pneumolysin in the mammal.

In some embodiments, the mammal is administered at least two, three, or more separate doses of the expression vector. The doses can optionally be separate by at least 1, 2, 3, 4, 5, 6, 7, or more days.

In some embodiments, the administration of the *S. pneumoniae* pneumolysin polypeptide or antigenic fragment thereof is at least 1, 2, 3, 4, 5, 6, 7, or more days after the administration of the expression vector.

In another aspect, the invention features a composition containing a polypeptide conjugated to a non-*Streptococcus pneumoniae* bacterial polysaccharide, wherein the polypeptide contains a fragment of at least 400 contiguous amino acids of a *Streptococcus pneumoniae* pneumolysin protein, wherein the polypeptide lacks the amino acid sequence KVEND (SEQ ID NO:22), wherein the polypeptide lacks hemolytic activity, and wherein the composition elicits an immune response against the non-*Streptococcus pneumoniae* bacterium when administered to a mammal. In some examples, the non-*Streptococcus pneumoniae* bacterium is selected from the group consisting of pneumococcus, *haemophilus influenza* type b, meningococcal group A, B or C, and group B streptococcus type Ia, Ib, II, III, V or VIII. Such a composition can be used to induce an immune response in a mammal by administering to the mammal an amount of the composition effective to induce an immune response against the non-*Streptococcus pneumoniae* bacterium in the mammal.

In another aspect, the invention features a purified antibody that binds (e.g., selectively binds) to a composition or polypeptide described herein. For example, an antibody may specifically bind to a composition containing a polypeptide conjugated to a *S. pneumoniae* capsular polysaccharide, wherein the polypeptide contains a fragment of at least 400 contiguous amino acids of a *S. pneumoniae* pneumolysin protein, wherein the polypeptide lacks the amino acid sequence KVEND (SEQ ID NO:22) (e.g., at the carboxy terminus), wherein the polypeptide lacks hemolytic activity, and wherein the composition elicits an immune response (e.g., a humoral immune response and/or a cellular immune response) against *S. pneumoniae* when administered to a mammal). Such an antibody can be, for example, a monoclonal or polyclonal antibody. Cell lines such as hybridomas can be prepared that secrete an antibody described herein. The antibody can be used to treat or prevent *Streptococcus pneumoniae* infection in a mammal by administering to the mammal a therapeutically or prophylactically effective amount of the purified antibody.

An advantage of the invention is that, in some embodiments, a first *S. pneumoniae* serotype polysaccharide-polypeptide conjugate can unexpectedly provide cross-protection against infection with a second *S. pneumoniae* serotype. Such cross-protection can increase the effectiveness of a given conjugate in treating or preventing infection by more than one *S. pneumoniae* serotype. Accordingly, protection against a plurality of *S. pneumoniae* serotypes can be provided without necessarily providing conjugates for every specific serotype.

Another advantage of the invention is that, in some embodiments, the pseudopneumolysin polypeptides lack hemolytic activity. Accordingly, such pseudopneumolysin conjugates and expression vectors have reduced or absent toxicity as compared to compositions containing a naturally occurring pneumolysin having hemolytic activity or a toxoided pneumolysin having partial hemolytic activity.

Another advantage of the invention is that, in some embodiments, expression vectors encoding pneumolysin truncates, as opposed to nucleic acids encoding pneumolysin point mutants, are unlikely to revert so as to encode a toxic protein having hemolytic activity. Because the pneumolysin truncates lack a region of pneumolysin that contributes to the hemolytic activity, any mutations in the nucleotide sequence of the expression vector should be unable to regenerate the toxic activity.

Unless otherwise defined, all technical and scientific terms used herein have the same meaning as commonly understood by those of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of a conflict in terminology, the present specification will control. In addition, the described materials and methods are illustrative only and are not intended to be limiting.

Other features and advantages of the invention will be apparent from the following detailed description and the claims.

DETAILED DESCRIPTION OF THE INVENTION

Figure 1:
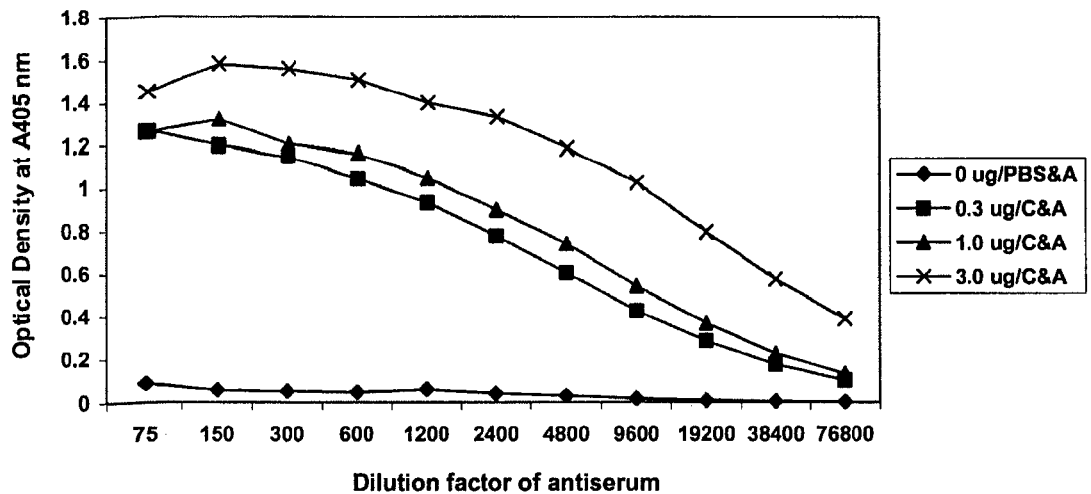
FIG. 1 is a graph depicting anti-pneumolysin IgG antibody production elicited in mice following immunization with a serotype 14 polysaccharide-pseudopneumolysin conjugate.
Figure 2:
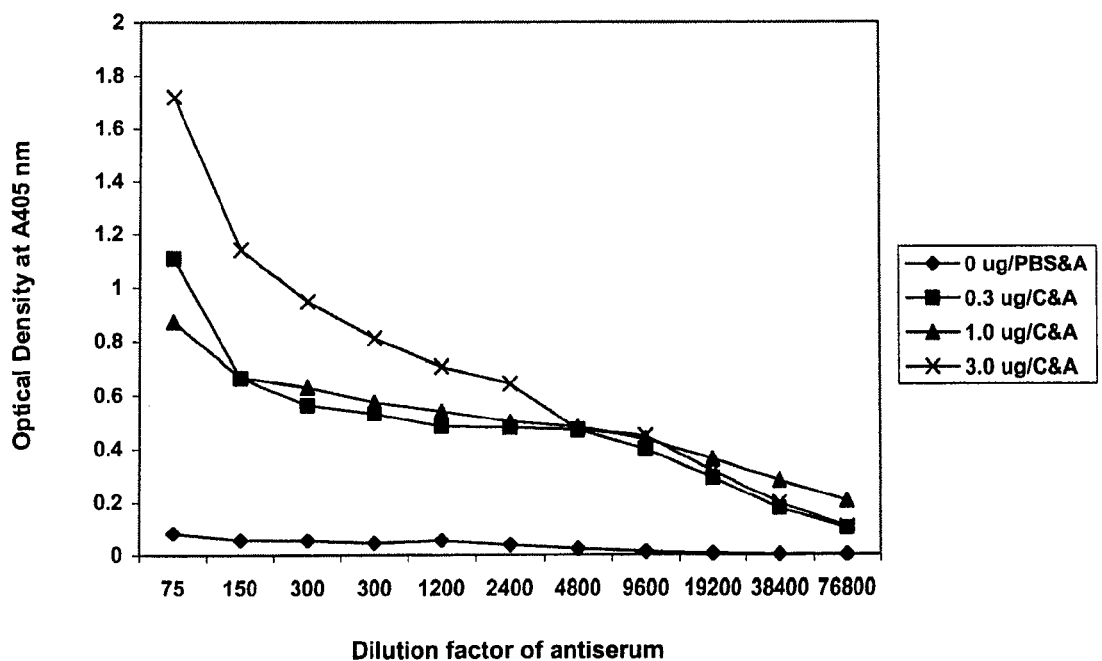
FIG. 2 is a graph depicting anti-polysaccharide IgG antibody production elicited in mice following immunization with a serotype 14 polysaccharide-pseudopneumolysin conjugate.
Figure 3:
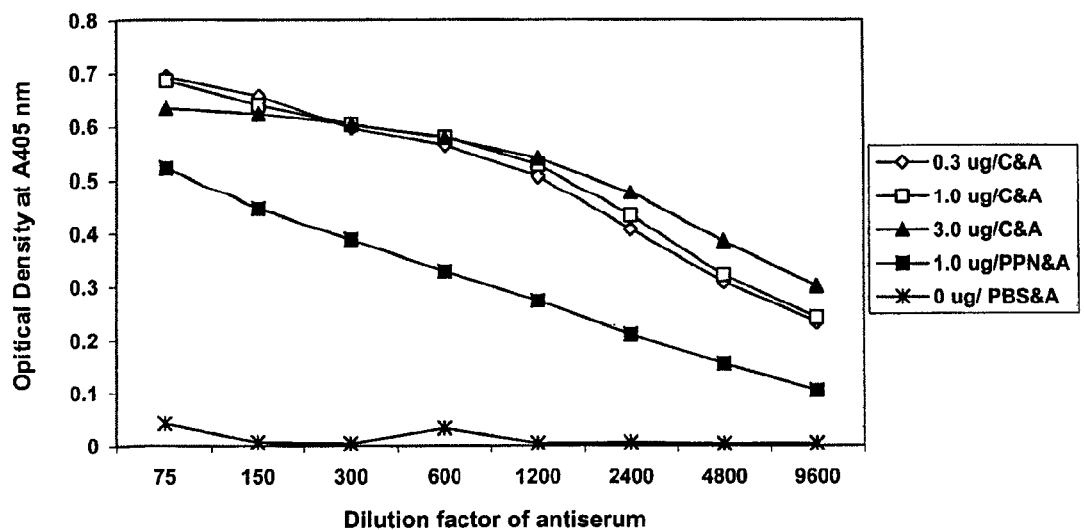
FIG. 3 is a graph depicting anti-pneumolysin IgG antibody production elicited in mice following immunization with a serotype 18C polysaccharide-pseudopneumolysin conjugate.
Figure 4:
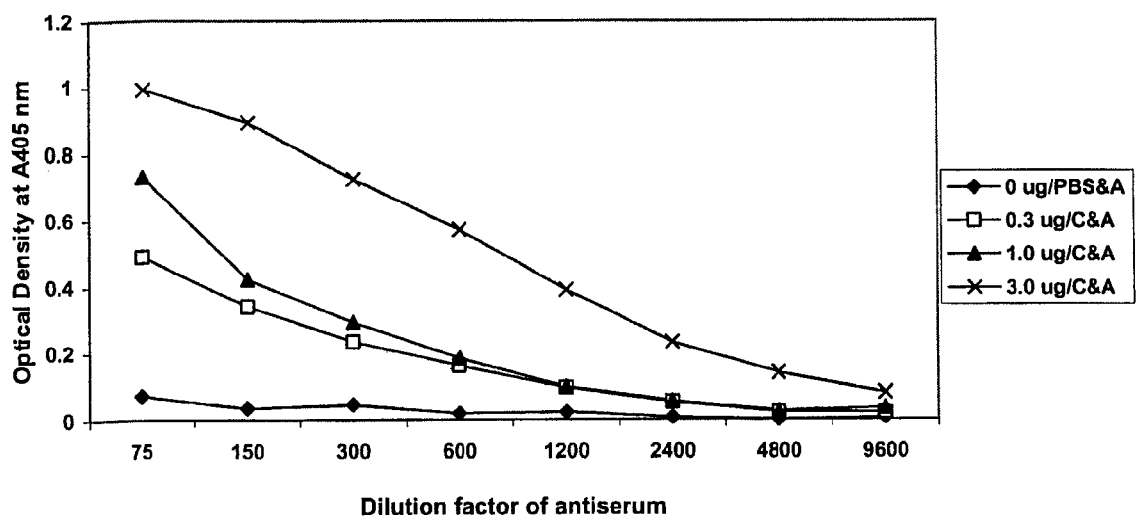
FIG. 4 is a graph depicting anti-polysaccharide IgG antibody production elicited in mice following immunization with a serotype 18C polysaccharide-pseudopneumolysin conjugate.
Figure 5:
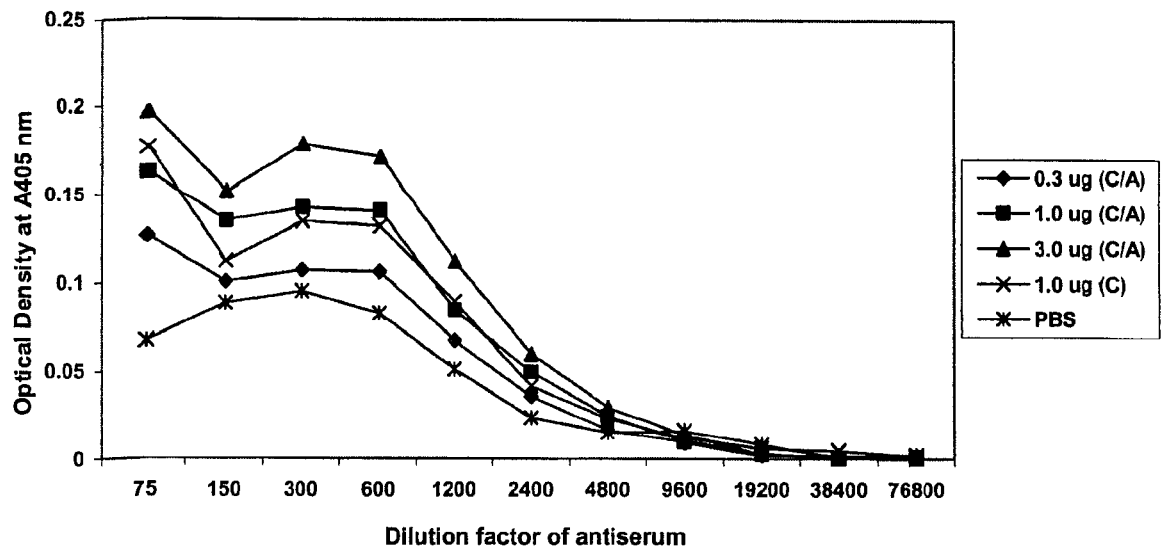
FIG. 5 is a graph depicting anti-pneumolysin IgG antibody production elicited in mice following immunization with a serotype 19F polysaccharide-pseudopneumolysin conjugate.

The present invention provides compositions and methods for treating or preventing pneumococcal infection. The polypeptides, polysaccharide-polypeptide conjugates, and expression vectors described herein, when administered to a mammal, induce an anti-pneumococcal immune response in the mammal. These compositions can be used prophylactically to vaccinate an individual and/or to therapeutically induce a therapeutic immune response in an infected individual.

Polysaccharide-Protein Conjugates

A polypeptide can be conjugated to a *S. pneumoniae* capsular polysaccharide by covalent or non-covalent methods. In general, the polypeptide component of the conjugate: contains either a portion of a *S. pneumoniae* pneumolysin protein or a mutated *S. pneumoniae* pneumolysin protein; lacks the amino acid sequence KVEND (SEQ ID NO:22); and lacks hemolytic activity. The polysaccharide-polypeptide conjugate elicits an immune response against *S. pneumoniae* when administered to a mammal. The immune response can be directed against the polypeptide, the polysaccharide, or the combination of the polypeptide and the polysaccharide.

The polypeptide component of the conjugate can be prepared using recombinant DNA technology, purified from natural sources, or synthesized chemically. In general, the polypeptide component differs in amino acid sequence from a naturally occurring *S. pneumoniae* pneumolysin protein. The sequence of the *S. pneumoniae* type 19A pneumolysin polypeptide is depicted in SEQ ID NO:1 (see Example 1). Exemplary polypeptide components of a conjugate include, but are not limited to amino acids 1-460, 1-461, 1-462, 1-463, 1-464, 1-465, 1-466, 1-469, and 1-470 of SEQ ID NO:1

Nucleic acids encoding truncated and/or mutated forms of a *S. pneumoniae* pneumolysin protein can be prepared, for example, by polymerase chain reaction (PCR). Nucleic acids encoding such proteins can be chosen for having codons, which are preferred or non-preferred, for a particular expression system. For example, the nucleic acid can be one in which at least one codon, preferably at least 10%, or 20% of the codons have been altered such that the sequence is optimized for expression in *E. coli*, yeast, human, insect, or CHO cells.

Nucleic acids encoding truncated and/or mutated forms of a *S. pneumoniae* pneumolysin protein can be fused to nucleotide sequences encoding (1) other pneumococcal proteins, such as autolysin, surface protein A, neuraminidase, hyaluronate lysate, choline binding protein A, or (2) non-pneumococcal proteins from organisms such as *hemophilus influenza* b, meningococcus group A, B, or C, or *streptococcus* group B. The nucleic acids encoding such fused protein are expressed in the expression systems.

Pneumolysin truncates can be useful carriers of polysaccharides, as hosts may lacking pre-existing antibodies to such a carrier polypeptide. Pneumolysin is a virulence factor in pneumococcal infections and there is little antigenic variation of the pneumolysin among pneumococci with different subtypes.

The polysaccharide-protein conjugate, when administered to a mammal such as a human, induces immune response that exceeds in magnitude, type, and/or duration the immune response induced by administration to a mammal of only the polysaccharide component. Accordingly, the polypeptide component must be of a length sufficient to induce such an enhanced immune response. For fragments of a naturally occurring *S. pneumoniae* pneumolysin protein, the fragments are at least 8, 10, 25, 50, 75, 100, 125, 150, 175, 200, 250, 300, 350, 400, 425, 450, 460, 465, 460, 465, or more amino acids in length. For polypeptides, varying in sequence from a naturally occurring *S. pneumoniae* pneumolysin protein, the polypeptide can be at least about 50%, 55%, 60%, 65%, 70%, 75%, 80%, 85%, 90%, 95%, 98% or more identical to a naturally occurring *S. pneumoniae* pneumolysin protein, e.g., SEQ ID NO:1

The polypeptide component preferably lacks hemolytic activity present in a naturally occurring *S. pneumoniae* pneumolysin protein. Generally, the polypeptide component exhibits less than 30%, 20%, 10%, 5%, 1%, or less of the hemolytic activity of a naturally occurring *S. pneumoniae* pneumolysin protein. Hemolytic activity can be measured as detailed in Example 3. In general, the hemolytic activity of a polypeptide can be determined by incubating the polypeptide with red blood cells, e.g., sheep erythrocytes, and measuring hemolysis induced by the polypeptide (see, e.g., Owen et al. (1994) FEMS Microbiology Letters 121:217-222 for a description of an exemplary hemolytic assay).

The polysaccharide component of the conjugate can be any *S. pneumoniae* capsular polysaccharide, including but not limited to, any of subtypes 1, 2, 3, 4, 5, 6B, 7F, 8, 9N, 9V, 10A, 11A, 12F, 14, 15B, 17F, 18C, 19A, 19F, 19A, 20, 22F, 23A, 23F, 24F, 27, 33F, or 34. In some embodiments, the capsular polysaccharide is selected from subtypes 4, 6B, 9V, 14, 18C, 19F, or 23F. In some embodiments, the polysaccharide is serotype 14. In other embodiments, the polysaccharide is serotype 18C. One or more of different capsular polysaccharides can be conjugated to a single polypeptide or a plurality of polypeptides. For example, a multivalent conjugate can include at least 1, 2, 3, 4, 5, 6, 7, 8, 9, or 10 different capsular polysaccharides. Polysaccharides can be conjugated to polypeptides, for example, via a monomeric linkage (only one end of the polysaccharide is attached to the polypeptide), a looped linkage (a single polypeptide is attached to looped polysaccharides), or cross-linked (multiple polysaccharides attached to multiple polypeptides).

Methods for the purification of polypeptides, e.g., pseudopneumolysin polypeptides described in the examples, and the conjugation of polysaccharides to polypeptides are described in Example 4. Additional details concerning polypeptide or polysaccharide purification and conjugation processes are described in, e.g., U.S. Pat. Nos. 4,242,501; 4,686,102; 5,623,057; and 5,565,204.

The conjugates or polypeptides described herein can be administered to a mammal to elicit an immune response (a prophylactic and/or therapeutic immune response) against *S. pneumoniae* in the mammal. A pharmaceutical composition containing a conjugate or polypeptide can be delivered in a pharmaceutically acceptable carrier, buffer, or preservative which is suitable for a vaccine including, but not limited to physiological saline or other injectable liquids. Additives customary in vaccines may also be present, for example stabilizers such as lactose or sorbitol, and adjuvants to enhance the immunogenic response such as aluminum phosphate, hydroxide, or sulphate and stearyl tyrosine. The vaccine produced may also be used as components of multivalent vaccines which elicit an immune response against a plurality of infectious agents.

The compositions can be administered in any manner known in the art, e.g., orally intramuscularly, intravenously, intraarterially, intrathecally, intradermally, intraperitoneally, intranasally, intrapulmonarily, intraocularly, intravaginally, intrarectally or subcutaneously. They can be introduced into the gastrointestinal tract or the respiratory tract, e.g., by inhalation of a solution or powder containing the conjugates. In some embodiments, the compositions can be administered via a skin patch.

A pharmaceutical composition (e.g., a vaccine) is administered in an amount sufficient to elicit production of antibodies as part of an immunogenic response. Dosage for any given patient depends upon many factors, including the patient's size, general health, sex, body surface area, age, the particular compound to be administered, time and route of administration, and other drugs being administered concurrently. Determination of optimal dosage is well within the abilities of a pharmacologist of ordinary skill.

The ability of a composition to elicit an immune response in a host mammal can be assayed by using methods for measuring immune responses that are well known in the art. For example, the generation of cytotoxic T cells can be demonstrated in a standard $^{51}$Cr release assay, by measuring intracellular cytokine expression or secretion, or by using major histocompatibility complex (MHC) tetramers. Standard assays, such as enzyme-linked immunosorbent assay (ELISA) or enzyme-linked immunospot (ELISPOT), can be used to measure cytokine profiles attributable to T cell activation. T cell proliferation can be measured using assays such as $^3$H-thymidine uptake and other assays known in the art. B cell responses can be measured using art recognized assays such as ELISA. Other methodologies can also be used to evaluate the effects of the conjugates on pathogen-associated lesions or on other pathogen levels generally (e.g., pneumococci clearance in challenged mice treated with the conjugate).

The composition described herein can be used in the manufacture of a medicament for the prevention or treatment of an infection with *S. pneumoniae* or conditions associated with such infection.

Antibodies

Antibodies directed against a polysaccharide, pneumolysin, or a combination thereof may be used in a prophylactic or therapeutic application to confer immunity from a first individual to a second individual (e.g., to augment the second individual's immune response against *S. pneumoniae* or to provide a response if the second individual is an immunocompromised patient). Antibodies directed against a polysaccharide, pneumolysin, or a combination thereof can be generated in an immunocompetent host (e.g., by administering to the immunocompetent host a conjugate described herein), harvested from the host and transfused into a recipient in need of treatment or prophylaxis, thereby conferring resistance to the recipient against not only the pneumolysin toxin, but also against *S. pneumoniae* and any possibly other bacteria which bind antibodies elicited by the conjugate (e.g., the polysaccharide component of the conjugate).

Antibodies elicited by a composition described herein can be formulated as a pharmaceutical composition and be used to confer a prophylactic or therapeutic immune response to an individual. Suitable components and methods of administration for pharmaceutical compositions are described herein. For eliciting passive immunity, the pharmaceutical composition may contain polyclonal antibodies or monoclonal antibodies or their derivatives of fragments. A pharmaceutical composition contains a prophylactically or therapeutically effective amount of an antibody, fragment, or derivative, as determined by standard clinical techniques.

Nucleic Acids Encoding Pneumococcal Polypeptides

Nucleic acids encoding a pneumococcal polypeptide or a fragment or variant of pneumococcal polypeptide can be administered to a mammal (e.g., a human) to generate a prophylactic and/or therapeutic immune response in the mammal. The immune response can be an anti-pneumococcal humoral and/or a cellular immune response.

Polypeptides that can be encoded by the nucleic acid constructs include the polypeptide components of the conjugates described herein, pseudopneumolysin polypeptides described in the examples, as well as autolysin and pneumococcal surface protein A and fragments and variants thereof. In addition, a nucleic acid can encode a combination of two or more such polypeptides, fragments, or variants.

Nucleic acid expression constructs can be prepared by using standard recombinant DNA methods. Regulatory elements can be included in a construct to facilitate expression of the nucleic acid encoding the polypeptide. These elements include sequences for enhancing expression in human or other mammalian cells, e.g., promoters, RNA stabilization sequences 5' and/or 3' to the coding sequence, introns (which can be placed at any location within or adjacent to the encoded sequence), and poly(A) addition sites, as well as an origin of replication and one or more genes encoding selectable markers enabling the constructs to replicate and be selected in prokaryotic and/or eukaryotic hosts. A T7 polymerase promoter or other type of promoter (e.g., a tissue-specific promoter or a cell-specific promoter such as a muscle-specific promoter) is optionally present at the 5' end of the coding sequence, and a sequence encoding a FLAG or other mAb determinant is optionally present at the 3' end of the coding sequence. The construct may also contain other transcriptional and translational signals, such as a Kozak sequence.

The construct may in addition include a sequence encoding a targeting signal that directs the encoded polypeptide to a desired intracellular compartment, the targeting signal being linked to the polypeptide. Targeting signals can direct the encoded polypeptide to endoplasmic reticulum (ER), the golgi, the nucleus, a lysosome, a class II peptide loading compartment, or an endosome, and include signal peptides, ER retention peptides, and lysosome-targeting peptides.

The nucleic acids can be used in any vector that allows for expression in cells of a mammal. The vector can be, e.g., a non-viral vector such as a plasmid or bacterial vector, an integrating viral vector, or a non-integrating viral vector. An example of a suitable vector is the family of pcDNA mammalian expression vectors (Invitrogen), which permit direct and rapid cloning of PCR products.

Various delivery systems can be used to deliver nucleic acids encoding polypeptides into appropriate cells. The nucleic acids encoding the polypeptides can be delivered in a pharmaceutically acceptable carrier such as saline, or as colloidal suspensions, or as powders, with or without diluents. The nucleic acids can be "naked" or associated with delivery vehicles and delivered using delivery systems known in the art, such as lipids, liposomes, microspheres, microparticles or microcapsules, gold particles, ISCOMS, nanoparticles, polymers, condensing agents, polysaccharides, polyamino acids, dendrimers, saponins, QS21, adsorption enhancing materials, adjuvants, or fatty acids. Nucleic acids can also be delivered to a cell, e.g., a skeletal muscle cell, either in vitro or in vivo, using electroporation.

The nucleic acids can be administered using standard methods, e.g., those described in Donnelly et al., J. Immunol. Methods 176:145, 1994, and Vitiello et al., J. Clin. Invest. 95:341, 1995, and can be delivered into subjects in any manner known in the art, e.g., orally intramuscularly, intravenously, intraarterially, intrathecally, intradermally, intraperitoneally, intranasally, intrapulmonarily, intraocularly, intravaginally, intrarectally or subcutaneously. They can be introduced into the gastrointestinal tract or the respiratory tract, e.g., by inhalation of a solution or powder containing the nucleic acids. Administration can be local or systemic.

It is expected that a dosage of approximately 100-2000 µg of nucleic acid would be administered to an individual. Where the patient is an adult human, vaccination regimens can include, e.g., intramuscular, intradermal, inhalation, or subcutaneous administrations of 10-1000 µg of a plasmid DNA when delivered in a microparticle, or of about 10-2500 µg, e.g., 100 to 2000, or 500 to 1000 µg, of naked plasmid DNA delivered intramuscularly or intradermally, repeated 3-6 times. As is well known in the medical arts, dosage for any given patient depends upon many factors, including the patient's size, general health, sex, body surface area, age, the particular compound to be administered, time and route of administration, and other drugs being administered concurrently. Determination of optimal dosage is well within the abilities of a pharmacologist of ordinary skill.

Other standard delivery methods, e.g., biolistic transfer or ex vivo treatment, can also be used. In ex vivo treatment, antigen presenting cells (APCs) such as dendritic cells, peripheral blood mononuclear cells, or bone marrow cells can be obtained from a patient or an appropriate donor and activated ex vivo with the nucleic acid, and then implanted or reinfused into the patient.

The nucleic acids can be administered alone or in combination with other therapies known in the art, e.g., antimicrobial agents. In addition, the nucleic acids can be administered in combination with other treatments designed to enhance immune responses, e.g., by co-administration with adjuvants, cytokines (or nucleic acids encoding cytokines), or CpG oligonucleotides, as is well known in the art.

The ability of a nucleic acid to elicit an immune response in a host mammal can be assayed by using methods for measuring immune responses that are well known in the art. For example, the generation of cytotoxic T cells can be demonstrated in a standard $^{51}$Cr release assay, by measuring intracellular cytokine expression or secretion, or by using MHC tetramers. Standard assays, such as ELISA or ELISPOT, can be used to measure cytokine profiles attributable to T cell activation. T cell proliferation can be measured using assays such as $^3$H-thymidine uptake and other assays known in the art. B cell responses can be measured using art recognized assays such as ELISA. Other methodologies can also be used to evaluate the effects of the nucleic acids on pathogen-associated lesions or on other pathogen levels generally (e.g., pneumococci clearance in challenged mice treated with the conjugate).

The nucleic acids described herein can be used in the manufacture of a medicament for the prevention or treatment of an infection with S. pneumoniae or conditions associated with such infection.

The invention will be further described in the following examples, which do not limit the scope of the invention described in the claims.

EXAMPLES

Example 1

Construction of Pseudopneumolysin Expression Vectors

Vectors for expressing truncated forms of a pneumolysin polypeptide are described in Examples 1A-1E. The encoded truncated polypeptides, termed "pseudopneumolysin" polypeptides, can be used for conjugation to pneumococcal polysaccharides for the preparation of conjugate vaccines. In addition, a nucleic acid encoding a pseudopneumolysin polypeptide can be administered to an individual to generate an immune response against the encoded polypeptide.

PCR was performed using S. pneumoniae type 19A chromosomal DNA as a template to amplify various fragments of the pneumolysin gene. The sense primer used for the PCR reaction annealed to the coding sequence of the pneumolysin gene just upstream of the translation initiation codon and incorporated a specific restriction enzyme site. The senses primer, designated LYSN-1 (5'-GACTAGATCTCCATATG-GCAAATAAAGCAGTAAATGAC-3'; SEQ ID NO:2), is complementary to nucleotides 1 to 24 at the 5' end of the pneumolysin gene. The antisense primer, designated LYSN-3 (5'-CAGTGGATCCTTACTAGTCATTTTCTACCTTATC-3'; SEQ ID NO:3), is complementary to pneumolysin nucleotides 1396 to 1413 at the 3' end of the pneumolysin gene. The primers amplify a 1413 base pair DNA encoding 471 amino acids of full length pneumolysin protein. The following is the amino acid sequence of the S. pneumoniae type 19A pneumolysin polypeptide:

```
                                         (SEQ ID NO:1)
MANKAVNDFILAMNYDKKKLLTHQGESIENRFIKEGNQLPDEFVVIERKK

RSLSTNTSDISVTATNDSRLYPGALLVVDETLLENNPTLLAVDRAPMTYS

IDLPGLASSDSFLQVEDPSNSSVRGAVNDLLAKWHQDYGQVNNVPARMQY

EKITAHSMEQLKVKFGSDFEKTGNSLDIDFNSVHSGEKQIQIVNFKQIYY

TVSVDAVKNPGDVFQDTVTVEDLKQRGISAERPLVYISSVAYGRQVYLKL

ETTSKSDEVEAAFEALIKGVKVAPQTEWKQILDNTEVKAVILGGDPSSGA
```

-continued

```
RVVTGKVDMVEDLIQEGSRFTADHPGLPISYTTSFLRDNVVATFQNSTDY

VETKVTAYRNGDLLLDHSGAYVAQYYITWNELSYDHQGKEVLTPKAWDRN

GQDLTAHFTTSIPLKGNVRNLSVKIRECTGLAWEWWRTVYEKTDLPLVRK

RTISIWGTTLYPQVEDKVEND.
```

PCR was generally performed as follows: 1 cycle at 94° C. for 4 minutes; 30 cycles at 94° C. for 1 minute, at 55° C. for 1 minutes, and at 72° C. for 1.5 minutes; and 1 cycle at 72° C. for 10 minutes. The PCR-synthesized DNA fragment was digested with NdeI and BamHI restriction enzymes and ligated into the pET11b expression vector (to generate pSA-14). The recombinant DNA was introduced into E. coli DE3 cells by transformation. Ampicillin-resistant transformants were selected. The presence of the insert was confirmed by digestion with NdeI and BamHI restriction enzymes.

The amplified DNA fragments lack nucleotides at the 3' end compared to wild type genomic sequence. Many of the pseudopneumolysin polypeptides encoded by these modified nucleic acids were found to be non-hemolytic and non-cytotoxic, but retain immunogenicity.

A. Construction of pSA-1 Expression Vector

The pSA-1 expression vector encodes a polypeptide consisting of amino acids 1-460 of the pneumolysin protein of SEQ ID NO:1. PCR was performed on S. pneumoniae type 19A chromosomal DNA using LSYN-1 (5'-GACTA-GATCTCCATATGGCAAATAAAGCAGTAAATGAC-3'; SEQ ID NO:2) and LSYN-4 (5'-GACTGGATCCTTACTA-GAGAGTTGTTCCCCAAATAG-3'; SEQ ID NO:5) primers to amplify a 1380 base pair DNA.

The PCR-synthesized DNA fragment was digested with NdeI and BamHI and ligated into the NdeI and BamHI sites of the pET11b expression vector to generate pSA-1. The recombinant DNA was introduced into E. coli DE3 cells by transformation. Ampicillin-resistant transformants were selected. The presence of the insert was confirmed by digestion with restriction enzymes, NdeI and BamHI and further confirmed by DNA sequencing.

The encoded 460 amino acid polypeptide, which lacks the 11 amino acids present at the carboxy terminus of the wild type pneumolysin protein, has the following sequence:

```
                      (amino acids 1-460 of SEQ ID NO:1)
MANKAVNDFILAMNYDKKKLLTHQGESIENRFIKEGNQLPDEFVVIERKK

RSLSTNTSDISVTATNDSRLYPGALLVVDETLLENNPTLLAVDRAPMTYS

IDLPGLASSDSFLQVEDPSNSSVRGAVNDLLAKWHQDYGQVNNVPARMQY

EKITAHSMEQLKVKFGSDFEKTGNSLDIDFNSVHSGEKQIQIVNFKQIYY

TVSVDAVKNPGDVFQDTVTVEDLKQRGISAERPLVYISSVAYGRQVYLKL

ETTSKSDEVEAAFEALIKGVKVAPQTEWKQILDNTEVKAVILGGDPSSGA

RVVTGKVDMVEDLIQEGSRFTADHPGLPISYTTSFLRDNVVATFQNSTDY

VETKVTAYRNGDLLLDHSGAYVAQYYITWNELSYDHQGKEVLTPKAWDRN

GQDLTAHFTTSIPLKGNVRNLSKIRECTGLAWEWWRTVYEKTDLPLVRKR

TISIWGTTL.
```

B. Construction of pSA-49 Expression Vector

The pSA-49 expression vector encodes a polypeptide consisting of amino acids 1-464 of the pneumolysin protein of SEQ ID NO:1. PCR was performed on S. pneumoniae type 19A chromosomal DNA using LSYN-1 (5'-GACTA-GATCTCCATATGGCAAATAAAGCAGTAAATGAC-3'; SEQ ID NO:2) and LSYN-54 (5'-CTGAGGATCCTTAC-TATACCTGAGGATAGAGAGTTGTTC-3'; SEQ ID NO:25) primers to amplify a 1392 base pair DNA.

The PCR-synthesized DNA fragment was digested with NdeI and BamHI and ligated into the NdeI and BamHI sites of the pET11b expression vector to generate pSA-49. The recombinant DNA was introduced into E. coli DE3 cells by transformation. Ampicillin-resistant transformants were selected. The presence of the insert was confirmed by digestion with restriction enzymes, NdeI and BamHI and further confirmed by DNA sequencing.

The encoded 464 amino acid polypeptide, which lacks the 7 amino acids present at the carboxy terminus of the wild type pneumolysin protein, has the following sequence:

(amino acids 1-464 of SEQ ID NO:1)
MANKAVNDFILAMNYDKKKLLTHQGESIENRFIKEGNQLPDEFVVIERKK

RSLSTNTSDISVTATNDSRLYPGALLVVDETLLENNPTLLAVDRAPMTYS

IDLPGLASSDSFLQVEDPSNSSVRGAVNDLLAKWHQDYGQVNNVPARMQY

EKITAHSMEQLKVKFGSDFEKTGNSLDIDFNSVHSGEKQIQIVNFKQIYY

TVSVDAVKNPGDVFQDTVTVEDLKQRGISAERPLVYISSVAYGRQVYLKL

ETTSKSDEVEAAFEALIKGVKVAPQTEWKQILDNTEVKAVILGGDPSSGA

RVVTGKVDMVEDLIQEGSRFTADHPGLPISYTTSFLRDNVVATFQNSTDY

VETKVTAYRNGDLLLDHSGAYVAQYYITWNELSYDHQGKEVLTPKAWDRN

GQDLTAHFTTSIPLKGNVRNLSVKIRECTGLAWEWWRTVYEKTDLPLVRK

RTISIWGTTLYPQV.

C. Construction of pSA-11 Expression Vector

The pSA-11 expression vector encodes a polypeptide consisting of amino acids 1-466 of the pneumolysin protein of SEQ ID NO:1. PCR was performed on S. pneumoniae type 19A chromosomal DNA using LSYN-1 (5'-GACTA-GATCTCCATATGGCAAATAAAGCAGTAAATGAC-3'; SEQ ID NO:2) and LSYN-17 (5'-GACTGGATCCTTAC-TAATCTTCTACCTGAGGATAG-3'; SEQ ID NO:6) primers to amplify a 1398 base pair DNA.

The PCR-synthesized DNA fragment shown was digested with NdeI and BamHI and ligated into the NdeI and BamHI sites of the pET11b expression vector to generate pSA-11. The recombinant DNA was introduced into E. coli DE3 cells by transformation. Ampicillin-resistant transformants were selected. The presence of the insert was confirmed by digestion with restriction enzymes, NdeI and BamHI and further confirmed by DNA sequencing.

The encoded 466 amino acid polypeptide, which lacks the 5 amino acids present at the carboxy terminus of the wild type pneumolysin protein, has the following sequence:

(amino acids 1-466 of SEQ ID NO:1)
MANKAVNDFILAMNYDKKKLLTHQGESIENRFIKEGNQLPDEFVVIERKK

RSLSTNTSDISVTATNDSRLYPGALLVVDETLLENNPTLLAVDRAPMTYS

IDLPGLASSDSFLQVEDPSNSSVRGAVNDLLAKWHQDYGQVNNVPARMQY

EKITAHSMEQLKVKFGSDFEKTGNSLDIDFNSVHSGEKQIQIVNFKQIYY

-continued
TVSVDAVKNPGDVFQDTVTVEDLKQRGISAERPLVYISSVAYGRQVYLKL

ETTSKSDEVEAAFEALIKGVKVAPQTEWKQILDNTEVKAVILGGDPSSGA

RVVTGKVDMVEDLIQEGSRFTADHPGLPISYTTSFLRDNVVATFQNSTDY

VETKVTAYRNGDLLLDHSGAYVAQYYITWNELSYDHQGKEVLTPKAWDRN

GQDLTAHFTTSIPLKGNVRNLSVKIRECTGLAWEWWRTVYEKTDLPLVRK

RTISIWGTTLYPQVED.

D. Construction of pSA-32 Expression Vector

The pSA-32 expression vector encodes a polypeptide consisting of amino acids 1-469 of the pneumolysin protein of SEQ ID NO:1. PCR was performed on S. pneumoniae type 19A chromosomal DNA using LSYN-1 (5'-GACTA-GATCTCCATATGGCAAATAAAGCAGTAAATGAC-3'; SEQ ID NO:2) and LSYN-37 (5'-GACTGGATCCTTAC-TATTCTACCTTATCTTCTACCTGAG-3'; SEQ ID NO:7) primers to amplify a 1407 base pair DNA.

The PCR-synthesized DNA fragment was digested with NdeI and BamHI and ligated into the NdeI and BamHI sites of the pET11b expression vector to generate pSA-32. The recombinant DNA was introduced into E. coli DE3 cells by transformation. Ampicillin-resistant transformants were selected. The presence of the insert was confirmed by digestion with restriction enzymes, NdeI and BamHI and further confirmed by DNA sequencing.

The encoded 469 amino acid polypeptide, which lacks the 2 amino acids present at the carboxy terminus of the wild type pneumolysin protein, has the following sequence:

(amino acids 1-469 of SEQ ID NO:1)
MANKAVNDFILAMNYDKKKLLTHQGESIENRFIKEGNQLPDEFVVIERKK

RSLSTNTSDISVTATNDSRLYPGALLVVDETLLENNPTLLAVDRAPMTYS

IDLPGLASSDSFLQVEDPSNSSVRGAVNDLLAKWHQDYGQVNNVPARMQY

EKITAHSMEQLKVKFGSDFEKTGNSLDIDFNSVHSGEKQIQIVNFKQIYY

TVSVDAVKNPGDVFQDTVTVEDLKQRGISAERPLVYISSVAYGRQVYLKL

ETTSKSDEVEAAEEALIKGVKVAPQTEWKQILDNTEVKAVILGGDPSSGA

RVVTGKVDMVEDLIQEGSRFTADHPGLPISYTTSFLRDNVVATFQNSTDY

VETKVTAYRNGDLLLDHSGAYVAQYYITWNELSYDHQGKEVLTPKAWDRN

GQDLTAHFTTSIPLKGNVRNLSVKIRECTGLAWEWWRTVYEKTDLPLVR

KRTISIWGTTLYPQVEDKVE.

E. Construction of pSA-31 Expression Vector

The pSA-31 expression vector encodes a polypeptide consisting of amino acids 1-470 of the pneumolysin protein of SEQ ID NO:1. PCR was performed on S. pneumoniae type 19A chromosomal DNA using LSYN-1 (5'-GACTA-GATCTCCATATGGCAAATAAAGCAGTAAATGAC-3'; SEQ ID NO:2) and LSYN-38 (5'-GACTGGATCCTTAC-TAATTTTCTACCTTATCTTCTACCTGAG-3'; SEQ ID NO:8) primers to amplify a 1410 base pair DNA.

The PCR-synthesized DNA fragment was digested with NdeI and BamHI and ligated into the NdeI and BamHI sites of the pET11b expression vector to generate pSA-31. The recombinant DNA was introduced into E. coli DE3 cells by transformation. Ampicillin-resistant transformants were selected. The presence of the insert was confirmed by digestion with restriction enzymes, NdeI and BamHI and further confirmed by DNA sequencing.

The encoded 470 amino acid polypeptide, which lacks the 1 amino acid present at the carboxy terminus of the wild type pneumolysin protein, has the following sequence:

```
                    (amino acids 1-470 of SEQ ID NO:1)
MANKAVNDFILAMNYDKKKLLTHQGESIENRFIKEGNQLPDEFVVIERKK

RSLSTNTSDISVTATNDSRLYPGALLVVDETLLENNPTLLAVDRAPMTYS

IDLPGLASSDSFLQVEDPSNSSVRGAVNDLLAKWHQDYGQVNNVPARMQY

EKITAHSMEQLKVKFGSDFEKTGNSLDIDFNSVHSGEKQIQIVNFKQIYY

TVSVDAVKNPGDVFQDTVTVEDLKQRGISAERPLVYISSVAYGRQVYLKL

ETTSKSDEVEAAFEALIKGVKVAPQTEWKQILDNTEVKAVILGGDPSSGA

RVVTGKVDMVEDLIQEGSRFTADHPGLPISYTFFSFLRDNVVATFQNSTD

YVETKVTAYRNGDLLLDHSGAYVAQYYITWNELSYDHQGKEVLTPKAWDR

NGQDLTAHFTTSIPLKGNVRNLSVKIRECTGLAWEWWRTVYEKTDLPLVR

KRTISIWGTTLYPQVEDKVEN.
```

Example 2

Expression, Purification, and Characterization of Recombinant Pseudopneumolysin Polypeptides PCR products were cloned into pET expression vectors, as described in Example 1. Recombinant DNA was transformed into *E. coli* and transformants were selected on plates containing antibiotics. Inserted DNA sequences were confirmed by DNA sequencing. Recombinant *E. coli* was grown at 37° C. overnight and isopropylthio-β-D-galactoside (IPTG) was added to the culture as an inducer and the cells were grown continuously for three hours. The expressed recombinant polypeptide was evaluated by SDS-polyacrylamide gel electrophoresis (SDS-PAGE) stained with Coomassie blue. Recombinant polypeptides were purified using affinity chromatography and hemolytic activity was tested with a hemolysis assay using sheep or human red blood cells (as detailed in Example 3).

Example 3

Determination of Hemolytic Activity of Pseudopneumolysin Polypeptides

Hemolytic activity of the encoded polypeptides was determined according to the following protocol.

1) Prepare 2% suspension of human or sheep red blood cells. 0.2 mL of fresh blood cells is added into 10 mL of PBS (pH 7.2). Spin the suspension at 3000 rpm for 30 seconds and re-suspend the pellet in 10 mL of PBS three times.

2) Add 1 µg of polypeptide in 0.5 mL PBS (pH7.2) and mix with 0.5 mL of washed 2% of RBC suspension.

3) Incubate the mixture at 37° C. for 1 hour and then centrifuge at 10,000 rpm for 2 min in an Eppendorf microcentrifuge.

4) Measure optical density (OD) at 541 nm. Hemolysis activity was measured as the percentage of OD absorption compared to full length pneumolysin polypeptide.

As shown in Table 1, truncates of pneumolysin lacking the C-terminal 7, 6, 2, or 1 amino acids lacked hemolytic activity. A truncate lacking the C-terminal 5 amino acids demonstrated a partial loss of hemolytic activity.

TABLE 1

Hemolytic Activity of Full Length Pneumolysin and Pseudopneumolysin

| Construct | Portion of pneumolysin (a) | % Hemolytic activity(b) |
|---|---|---|
| pSA-14 | 1-471 (full length pneumolysin) | 100 |
| pSA-49 | 1-464 (−7 aa pseudopneumolysin) | 0 |
| pSA-48 | 1-465 (−6 aa pseudopneumolysin) | 0.2 |
| pSA-11 | 1-466 (−5 aa pseudopneumolysin) | 17 |
| pSA-34 | 1-467 (−4 aa pseudopneumolysin) | 100 |
| pSA-33 | 1-468 (−3 aa pseudopneumolysin) | 100 |
| pSA-32 | 1-469 (−2 aa pseudopneumolysin) | 0 |
| pSA-31 | 1-470 (−1 aa pseudopneumolysin) | 1.8 |

(a) Numbers represent amino acids (aa) from the native pneumolysin polypeptide absent in the C-terminal truncate.
(b) The hemolytic activities of the C-terminal truncates are expressed as a percentage of the full length construct, pSA-14.

Example 4

Preparation of Polysaccharide-Protein Conjugates

A. Oxidization of Polysaccharide

Pneumococcal capsular polysaccharides, such as 4, 6B, 9V, 14, 18, 19F, and 23F, were purchased from American Type Culture Collection (Manassas, Va.). 10 mg of polysaccharide was dissolved in 1 mL of distilled water at 4° C. overnight. One mL of 0.2 M PBS (pH 7.2) was added the next day. Polysaccharide was oxidized by reaction with 2 mM sodium periodate (MW: 213.9, Sigma) in the dark for 10 minutes at room temperature. Excess sodium periodate was destroyed by reaction with ethylene glycol (MW: 62.07) at a final concentration of 25 mM. The reaction mixture containing the polysaccharide was dialyzed extensively three times in 1000 mL 0.1 M PBS (pH 7.2).

B. Preparation of Immuno-Affinity Column (i) Purification of Full Length His-Tagged Pneumolysin

*E. coli* (pET24b containing C-His-tagged pneumolysin) was grown in 4 mL LB medium containing 40 µL of 20% glucose and 4 µL of 50 mg/mL kanamycin and incubated at 37° C. overnight with consistent shaking of 160 rpm. Three mL overnight culture was transferred into 100 mL LB medium containing 1 mL of 20% glucose and 100 µL of 50 mg/mL kanamycin and incubated at 37° C. with consistent shaking of 160 rpm until $OD_{600}$ reached 0.4-0.5. 400 µL of 1 M IPTG was added to 100 mL of culture with a final concentration of 4 mM of IPTG. Cells were harvested, 3 hours after inducing gene expression, by centrifugation at 4000 rpm for 5 minutes. Full length His-tagged pneumolysin was purified according to the protocol of ProBond Purification System provided by Invitrogen (Carlsbad, Calif.).

(ii) Production of Polyclonal Antibodies Against His-Tagged Pneumolysin

New Zealand white rabbits were injected with 4 equal doses of 25 µg each, at 4 different sites of emulsified His-tagged pneumolysin and TiterMax adjuvant (400 µL of 1 mg/mL His-tagged pneumolysin and 400 µL TiterMax adjuvant); one in each thigh muscle (i.m.) and one subcutaneously (s.c.) on each side of the spine over the longitudinal muscles of the back. After 14 days, 5 mL of blood was collected from the rabbits via ear veins.

If antibody titers from serum reached 1:3000 dilution levels, the animals were terminal bled out. If antibody titers were below 1:3000, a second dose of antigen was injected, and the animals were tested one week later (7 days after second dose). The cycles were continued until adequate titers were achieved.

(iii) Rabbit IgG Purification Using Affi-Gel Protein A Agarose

Serum from a rabbit immunized with His-tagged pneumolysin was applied to Affi-Gel protein A column equilibrated with 10 mM sodium phosphate and 150 mM NaCl (pH 8.2). After washing with 10 bed volumes, immunoglobulins were eluted with 2 to 5 volumes of 100 mM Na citrate (pH 3.0). The eluted IgG was collected, pooled and measured OD at 280. Three ml of purified IgG was further applied to 10 DG column and the first three ml eluted from the column was discarded. The column was added 3.5 mL of either coupling buffer (150 mM NaCl and 100 mM Na acetate pH 5.5) or 0.1M 3-(N-morpholino) propane-sulfonic acid) (MOPS) buffer. 3.5 ml eluant IgG was collected, pooled, and further coupled to either Affi-Gel Hz or Affi-Gel10.

(iv) Preparation of Immunoaffinity Column Using IgG Random Coupling to Affi-Ge10

Affi-Gel 10 is N-hydroxysuccinimide esters of a derivatized crosslinked agarose gel bead support and couples all ligands via primary amines. For coupling with IgG, Affi-Gel 10 was transferred to 15 mL tube and washed three times with cold $DDH_2O$ and two times with cold 0.1 M MOPS buffer (pH 7.0). Purified IgG was added to 15 mL tube containing pre-washed Affi-Gel 10 and rotated-over-end at 4° C. for four hr. The remaining active esters of Affi-Gel 10 was blocked by adding 100 mM Tris HCl pH 8.0 for another 0.5 hr at 4° C. The gel was transferred to 1.5×9.0 cm column. The column eluant was collected and measured OD at 280. The Affi-Gel 10 immunoaffinity column was washed with two bed volumes of 0.5M NaCl and 25 mM Tris HCl (pH 8.0). The column eluant was collected again and measured OD at 280. Based on the concentration of total IgG and uncoupled IgG, the coupling efficiency was calculated.

(v) Examination of Immunoaffininty Columns

For testing the immunoaffininty columns, the fractions with pseudopneumolysin from DEAE-Sepharose chromatography was added into 25 mM TrisHCl (pH8.0), 0.5 M NaCl and 0.5% Triton X-100. The sample was applied to 6.5 ml Affi-Gel 10 column (1.5×12 cm) equilibrated with 0.5 M NaCl and 25 mM Tris HCl (pH8.0) at flow rate of 1 mL/2 min. The flow through fraction was collected. The column was washed with 15 mL of 0.5 M NaCl and 25 mM Tris HCl (pH8.0) two to three times. The column was washed again with 5 mL of 4 M urea. The bound pseudopneumolysin protein was eluted with 7 mL of 4 M urea twice. Protein samples from first 7 mL of 4 M urea fractions were analyzed by 9% SDS-PAGE and visualized by staining with Coomassie brilliant blue R-20.

C. Preparation of Recombinant Pseudopneumolysin Protein

Bacteria transformed with expression vector pSA-49 (which encodes a polypeptide lacking the 7 amino acids at the C-terminus of pneumolysin; see Example 1) were grown in a 50 mL tube containing 30 mL LB medium with 100 μg/ml ampicillin at 37° C. overnight. The following morning, 400 mL of LB medium with 100 μg/mL ampicillin and 0.2% glucose in a 1 liter flask was inoculated with 13 ml of overnight culture and incubated with shaking at 37° C. At a cell density corresponding to an A600 of 0.5, the expression of the pseudopneumolysin protein was induced by addition of 2 or 4 mM IPTG for 3 hours.

Bacteria were centrifuged in a 500 mL centrifuge tube at 6,500 rpm for 10 minutes. The bacterial pellet was resuspended in 40 mL Tris HCl buffer (pH 8.0) with 100 μg/mL lysozyme, incubated on ice for 15 minutes, and sonicated 3 times with 10-second bursts on ice. The lysate was frozen at −80° C. for 10 min and thawed at 37° C. for 5 min. The cell lysate was treated by sonication-freezing-thawing two more times. Insoluble cell debris was removed by centrifugation at 6,000 rpm for 20 minutes. The supernatant lysate was further passed through 0.8 μM filter. The flow through proteins were examined by 9% SDS PAGE analysis and visualized by Coomassie brilliant blue R-250 staining. The crude lysate was further purified by DEAE-Sepharose chromatography.

Twenty mL crude bacterial lysate was loaded on a column (5×12 cm) with DEAE-Sepharose equilibrated with 25 mM Tris-HCl (pH 8.0). After the first flow through was collected, 10 mL of 25 mM Tri-HCl was added to the column. 10 mL of flow through was collected and pooled with the first flow through fraction (fraction 1). Next, 35 mL of 25 mM Tris-HCl (pH 8.0) was applied and the flow through was collected (fraction 2). Another 35 mL of 25 mM Tris-HCl (pH 8.0) was applied and the flow through was collected again (fraction 3). The bound bacterial proteins were eluted with 4 M NaCl and 25 mM Tris HCl (fraction 4). The protein concentration in each fraction was measured by reading OD at 280 nm. Protein samples were analyzed by 9% SDS-polyacrylamide gel electrophoresis (SDS-PAGE) and visualized by stained with Coomassie blue R-20. The flow through fractions (1 and 2) containing pseudopneumolysin were further purified by immunoaffinity chromatography.

After DEAE-Sepharose chromatography, the fractions with pseudopneumolysin were added to 25 mM Tris HCl (pH 8.0), 0.5 M NaCl and 0.5% Triton X-100. The sample was applied to 6.5 mL Affi-Gel 10 column coupled rabbit anti-pneumolysin IgG (1.5×12 cm) equilibrated with 0.5 M NaCl and 25 mM Tris HCl (pH 8.0) at flow rate of 1 mL/2 min. The flow through fraction was collected. The column was washed with 15 mL of 0.5 M NaCl and 25 mM Tris HCl (pH 8.0) three times. The column was washed again with 5 mL of 4 M urea. The bound pseudopneumolysin protein was eluted with 7 mL of 4 M urea twice. Protein samples from unbound and bound fractions were analyzed by SDS-PAGE and visualized by staining with Coomassie brilliant blue R-20.

After immunoaffinity chromatography, 4 M urea eluted fraction containing pseudopneumolysin was further purified by 10 DG chromatography to remove urea. A 3.0 mL sample was applied to 10 DG column (1.5×12 cm) equilibrated with 1×PBS buffer. The first 3.0 mL of flow through was discarded. The column was added a 3.9 mL of 1×PBS buffer. The 3.9 mL fraction collected from the column was measured OD at 280 and the protein fractions were collected. The purity of protein was evaluated by 9% SDS-polyacrylamide gel electrophoresis.

D. Preparation of Polysaccharide-Protein Conjugates

Two milligrams of *S. pneumoniae* polysaccharide 18C was conjugated to the pseudopneumolysin protein (described in section C above) by direct conjugation using a reductive amination assay. 10 mg of pseudopneumolysin in 0.1 M PBS was added to the oxidized polysaccharide reaction mix and incubated at room temperature with gentle stirring for 30 min. Sodium cyanoborohydride was added at the final concentration of 20 mM (e.g., 750 μL of 100 mM cyanoborohydride was added into 3 ml of oxidized polysaccharide and pseudopneumolysin mixture). The mixture was incubated at room temperature with gentle stirring for 5 days. The conjugate was precipitated at 9,000 rpm for 10 minutes and then dissolved in 1-2 mL 0.1 M PBS, pH 7.2. The mixture was chromatographed on Sepharose CL-4B column (1.5×100 cm) equilibrated with 1×PBS, pH 7.2. The fractions containing both protein and polysaccharide were pooled and concentrated by an Amicon Centricon-30 (molecular weight cutoff 30,000) and then assayed for protein and polysaccharide content.

Example 5

Antibody Response of Mice to the Polysaccharide-Protein Conjugates

The *S. pneumoniae* 14, 18C, 19F, 23F, 4, 6B and 9V polysaccharide-pseudopneumolysin protein conjugates prepared as described in Example 4 were tested for their ability to raise antibodies against polysaccharide and pneumolysin in mice. The conjugates, 0.3, 1, 3 µg/dose of polysaccharide mixed with aluminum hydroxide adjuvant (0.1 mg/dose), were injected intraperitoneally to groups of female NIH Swiss mice. In some experiments, a second group of mice received 1 µg of polysaccharide, and/or a third group of mice received 1 µg of pseudopneumolysin. Mice received two boosters at two weeks of intervals. At seven days after the final injection, the serum levels of anti-polysaccharide antibodies and anti-pneumolysin antibodies were measured. Table 2 is a summary of the specific conjugates administered and the immune responses measured in the experiments depicted in each of FIGS. 1-14.

TABLE 2

Summary of Conjugates Administered and Antibodies Detected in Mice Immunization Experiments

| Figure Number | Serotype of *S. pneumoniae* polysaccharide component of conjugate | Antibody Response Measured |
|---|---|---|
| 1 | 14 | anti-pneumolysin IgG antibody |
| 2 | 14 | anti-serotype14 polysaccharide IgG antibody |
| 3 | 18C | anti-pneumolysin IgG antibody |
| 4 | 18C | anti-serotype 18C polysaccharide IgG antibody |
| 5 | 19F | anti-pneumolysin IgG antibody |
| 6 | 19F | anti-serotype 19F polysaccharide IgG antibody |
| 7 | 23F | anti-pneumolysin IgG antibody |
| 8 | 23F | anti-serotype 23F polysaccharide IgG antibody |
| 9 | 4 | anti-pneumolysin IgG antibody |
| 10 | 4 | anti-serotype 4 polysaccharide IgG antibody |
| 11 | 6B | anti-pneumolysin IgG antibody |
| 12 | 6B | anti-serotype 6B polysaccharide IgG antibody |
| 13 | 9V | anti-pneumolysin IgG antibody |
| 14 | 9V | anti-serotype 9V polysaccharide IgG antibody |

The following abbreviations are used in the legends of FIGS. 1-14: Phosphate Buffered Saline ("PBS"); Conjugates ("C"); Aluminum Hydroxide Adjuvant ("A"); and Pseudopneumolysin ("PPN").

Figure 6:
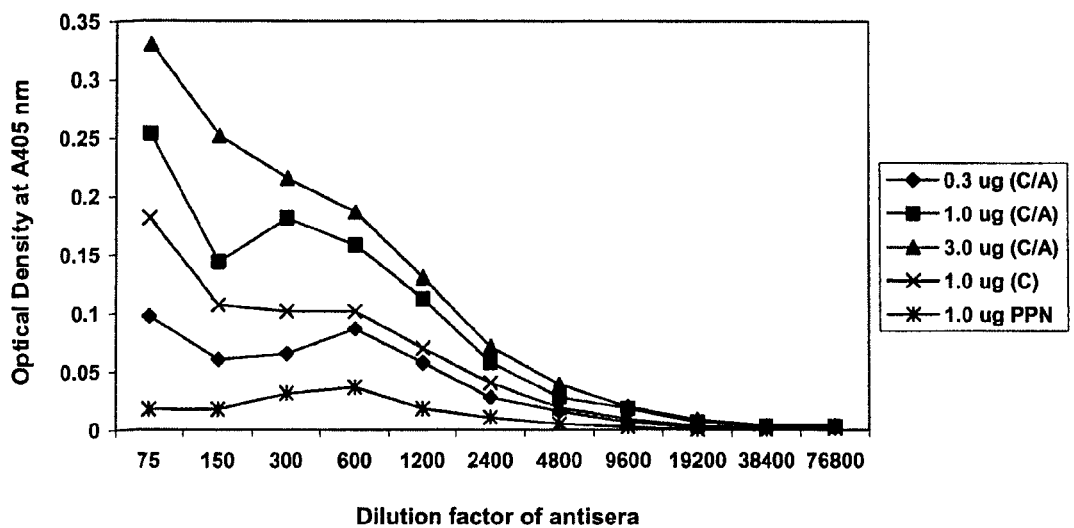
FIG. 6 is a graph depicting anti-polysaccharide IgG antibody production elicited in mice following immunization with a serotype 19F polysaccharide-pseudopneumolysin conjugate.
Figure 7:
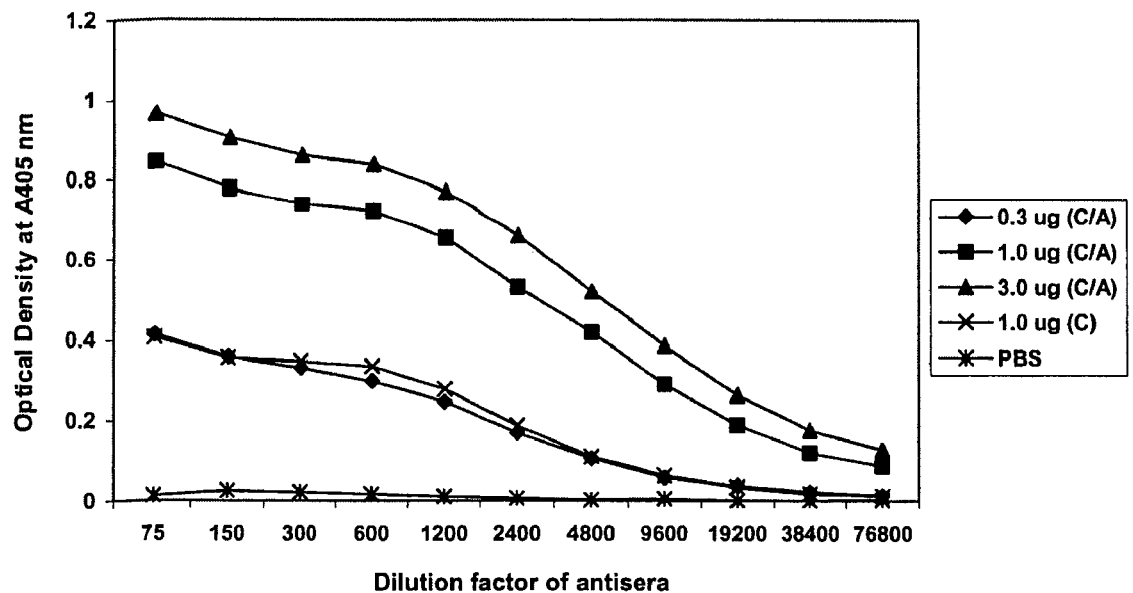
FIG. 7 is a graph depicting anti-pneumolysin IgG antibody production elicited in mice following immunization with a serotype 23F polysaccharide-pseudopneumolysin conjugate.
Figure 8:
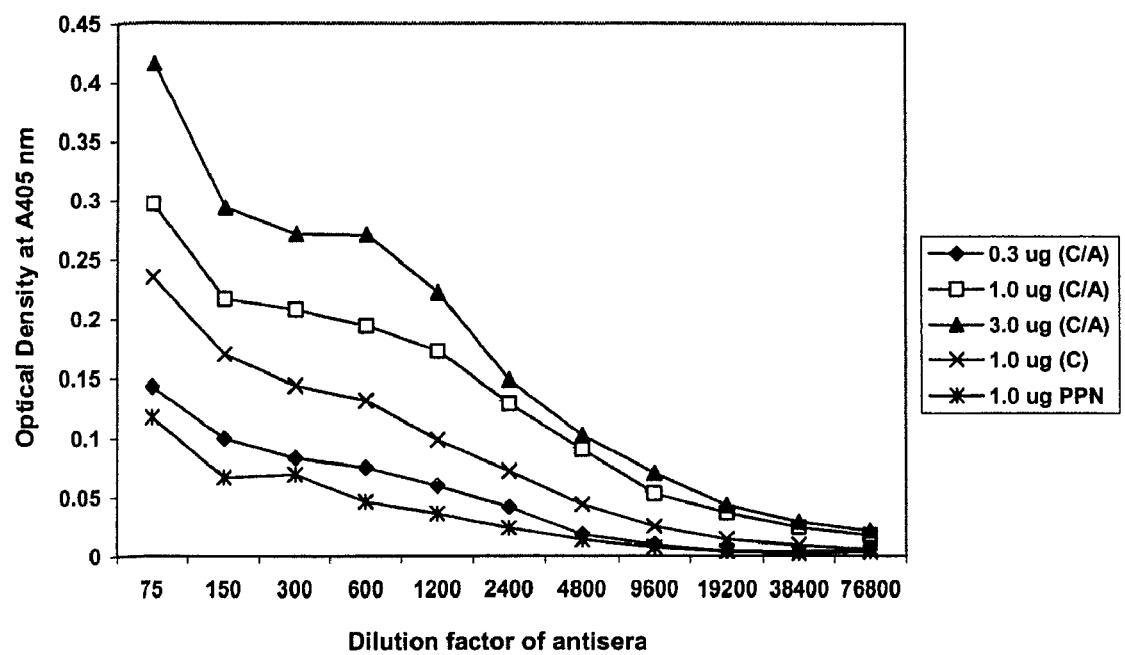
FIG. 8 is a graph depicting anti-polysaccharide IgG antibody production elicited in mice following immunization with a serotype 23F polysaccharide-pseudopneumolysin conjugate.
Figure 9:
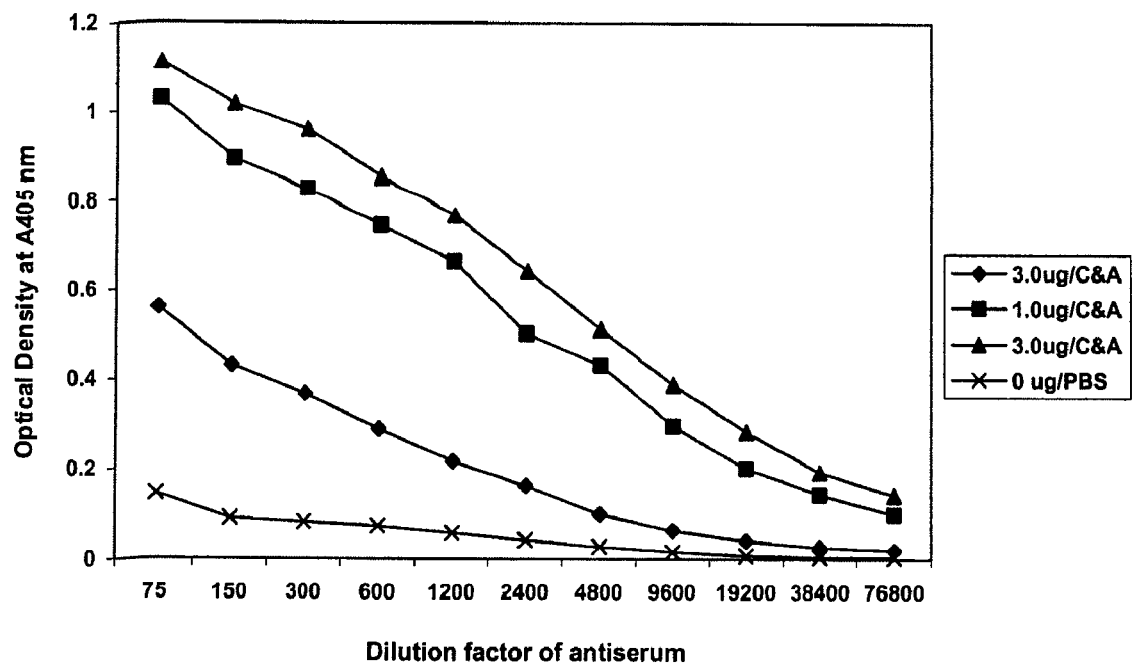
FIG. 9 is a graph depicting anti-pneumolysin IgG antibody production elicited in mice following immunization with a serotype 4 polysaccharide-pseudopneumolysin conjugate.
Figure 10:
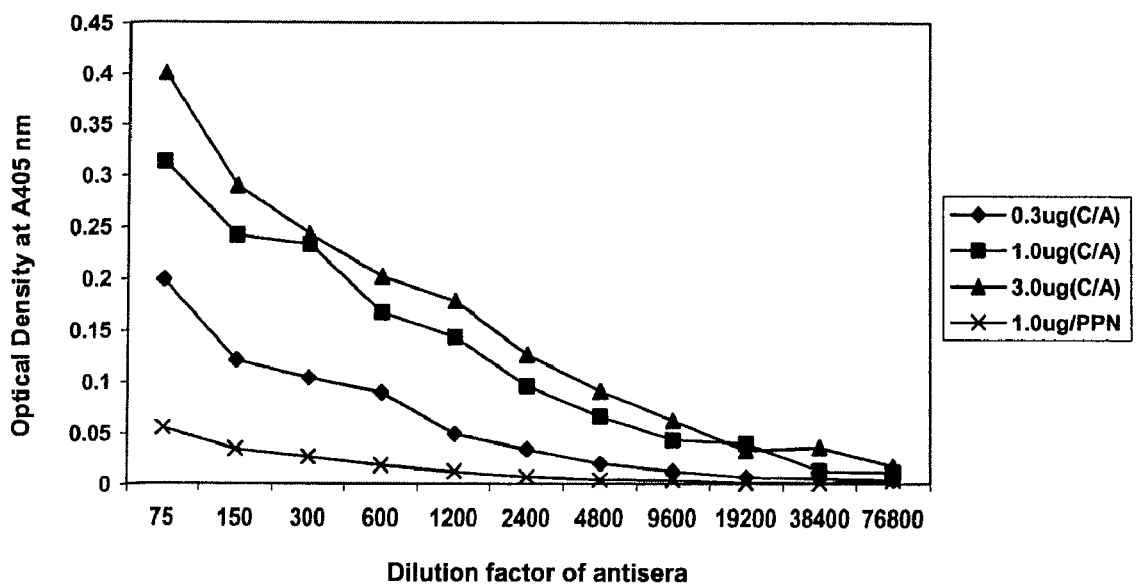
FIG. 10 is a graph depicting anti-polysaccharide IgG antibody production elicited in mice following immunization with a serotype 4 polysaccharide-pseudopneumolysin conjugate.
Figure 11:
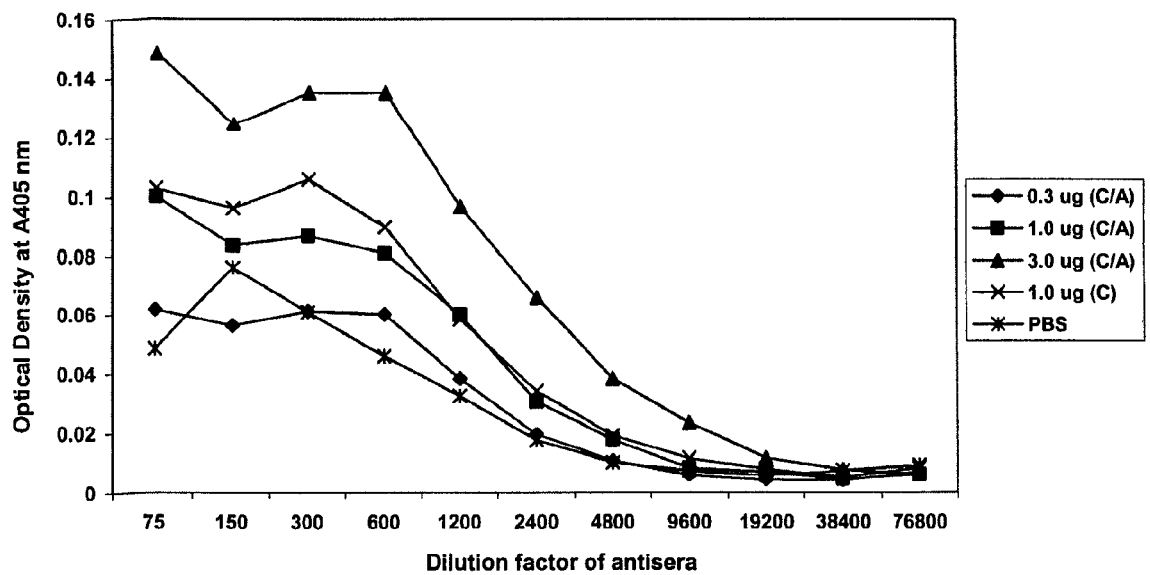
FIG. 11 is a graph depicting anti-pneumolysin IgG antibody production elicited in mice following immunization with a serotype 6B polysaccharide-pseudopneumolysin conjugate.
Figure 12:
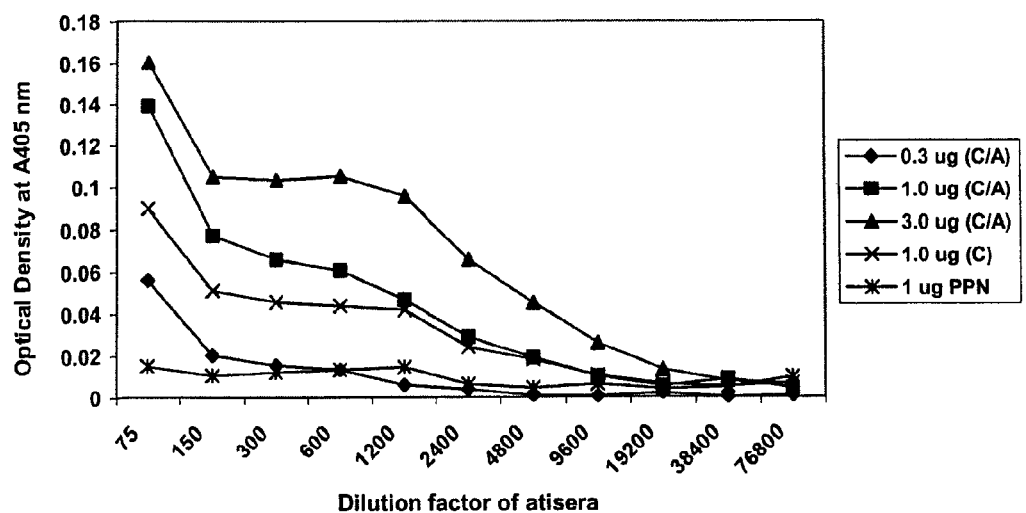
FIG. 12 is a graph depicting anti-polysaccharide IgG antibody production elicited in mice following immunization with a serotype 6B polysaccharide-pseudopneumolysin conjugate.
Figure 13:
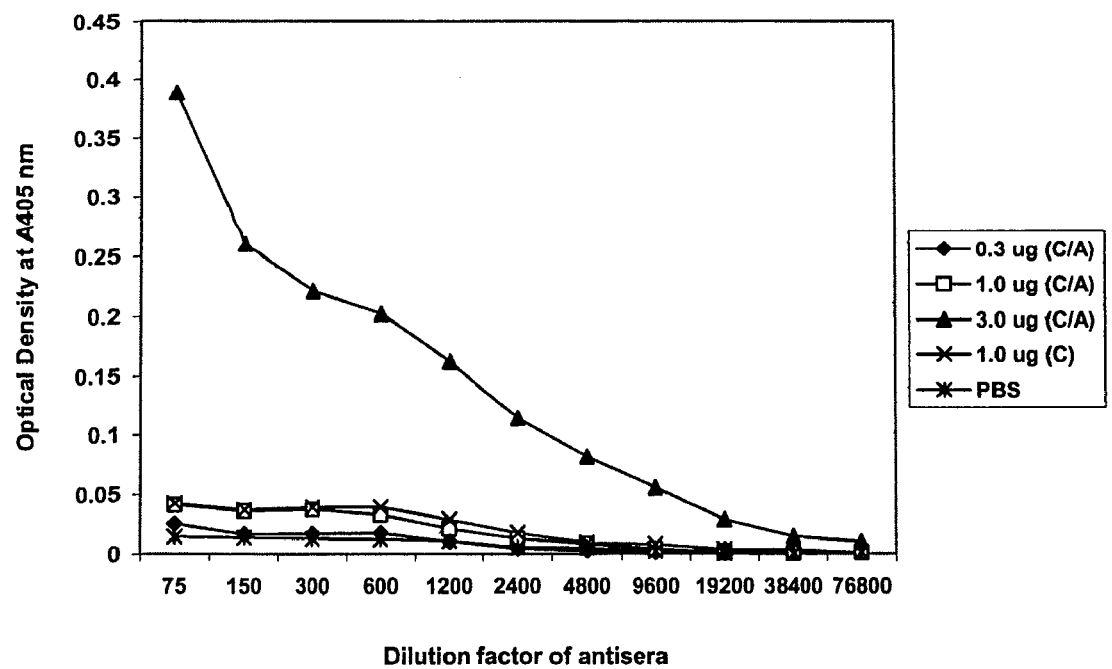
FIG. 13 is a graph depicting anti-pneumolysin IgG antibody production elicited in mice following immunization with a serotype 9V polysaccharide-pseudopneumolysin conjugate.
Figure 14:
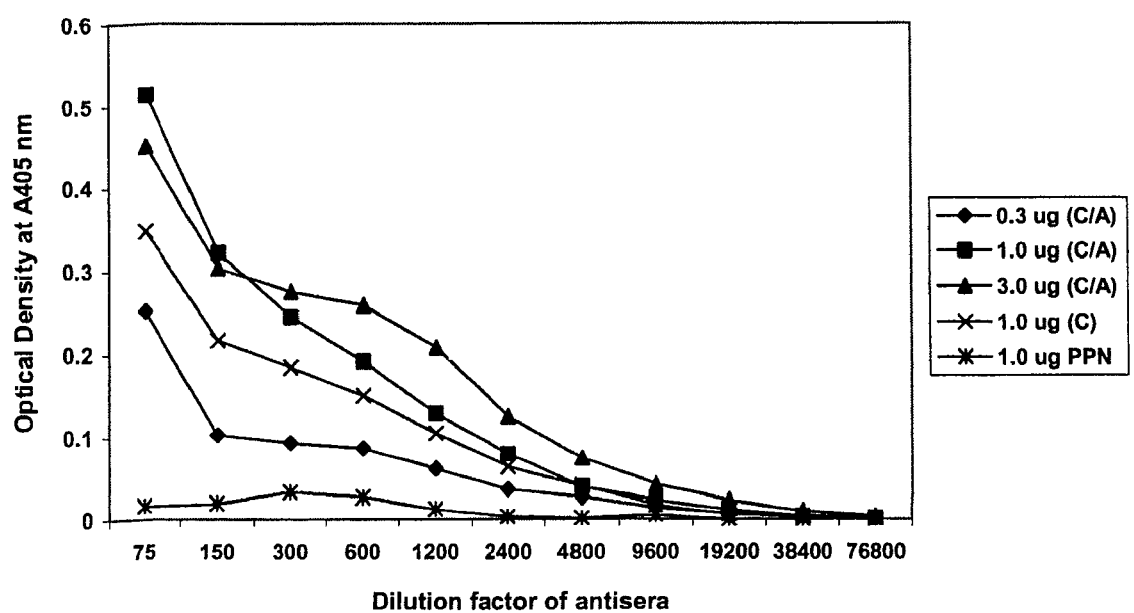
FIG. 14 is a graph depicting anti-polysaccharide IgG antibody production elicited in mice following immunization with a serotype 9V polysaccharide-pseudopneumolysin conjugate.

Mice immunized with the polysaccharide-pseudopneumolysin conjugate showed an induction of antibodies that reacted by ELISA with His-tagged wild-type pneumolysin. For all groups receiving the conjugate and adjuvant, the anti-pneumolysin and anti-polysaccharide antibody levels were significantly greater than the PBS and adjuvant control ($p<0.001$, t-test). The serum of the conjugate-administered mice exhibited unexpectedly high titers of anti-pneumolysin and anti-polysaccharide antibodies, at serum dilution factors of 76800 and 9600 respectively, as compared to mice administered the PBS alone. The highest anti-pneumolysin and anti-polysaccharide antibody levels were observed in mice that received 3.0 µg of the polysaccharide-pseudopneumolysin conjugate (FIGS. 1-14). Anti-pneumolysin antibody levels were higher in the groups that received the polysaccharide-pseudopneumolysin conjugate with adjuvant, as compared to the pseudopneumolysin with the adjuvant group (FIG. 3) or the pseudopneumolysin without adjuvant group (FIG. 6).

Tables 3 and 4 show that mice that received 3.0 µg of the conjugate had the highest percentage of responders. These results indicate that the effectiveness of pneumococcal vaccine can be improved by the conjugate of polysaccharide to a pseudopneumolysin protein. In addition to the antibody response, cross protective immunity and bacterial clearance were examined in mice administered the conjugate vaccines (see Example 8).

TABLE 3

Percentage of Mice With Positive Response Against 18C Polysaccharide

| Groups of Mice | Percentage of Positive Responders |
|---|---|
| Aluminum Hydroxide Adjuvant | 0% |
| 1 µg Pseudopneumolysin (PPN) | 0% |
| 1 µg 18C Polysaccharide(PS) + Adjuvant | 0% |
| 0.3 µg 18C (PS)-PPN Conjugate + Adjuvant | 60% |
| 1.0 µg 18C (PS)-PPN Conjugate + Adjuvant | 75% |
| 3.0 µg 18C (PS)-PPN Conjugate + Adjuvant | 100% |
| 1.0 µg 18 C (PS)-PPN Conjugate without Adjuvant | 20% |

Note:
The positive responder was determined using 1:100 dilution of serum samples from all the mice. An A405 nm optical reading greater than 0.05 indicated a positive response.

TABLE 4

Percentage of Mice With Positive Response Against 14 Polysaccharide

| Groups of Mice | Percentage of Positive Responders |
|---|---|
| Aluminum Hydroxide Adjuvant | 0% |
| 1 µg Pseudopneumolysin (PPN) | 0% |
| 1 µg 14 Polysaccharide(PS) + Adjuvant | 0% |
| 0.3 µg 14 (PS)-PPN Conjugate + Adjuvant | 100% |
| 1.0 µg 14 (PS)-PPN Conjugate + Adjuvant | 100% |
| 3.0 µg 14 (PS)-PPN Conjugate + Adjuvant | 100% |
| 1.0 µg 14 (PS)-PPN Conjugate without Adjuvant | 20% |

Note:
Positive responses were determined using 1:300 dilution of serum samples from all the mice. An A405 nm optical reading greater than 0.12 indicated a positive response.

Figure 15:
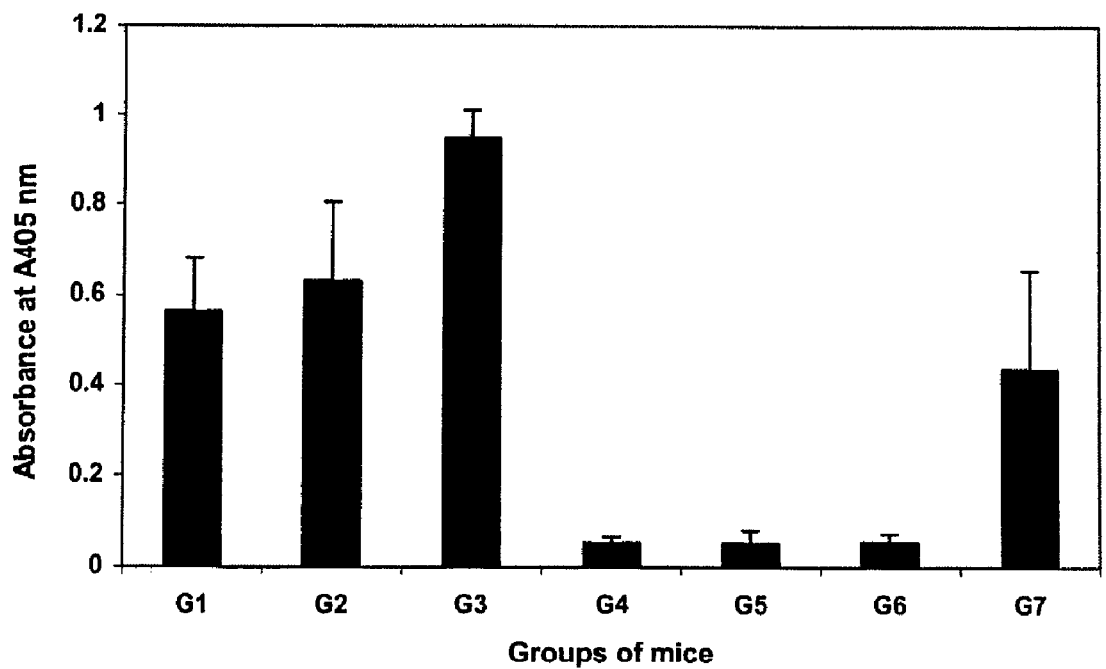
FIG. 15 is a graph depicting the antibody response to *S. pneumoniae* serotype 14 polysaccharide after a third injection of *S. pneumoniae* serotype 14 polysaccharide-pseudopneumolysin conjugate.

FIG. 15 is a graph depicting the antibody response in mice to serotype 14 polysaccharide 7 days after the third injection of the serotype 14 polysaccharide-pseudopneumolysin conjugate. In FIG. 15, G1, G2, and G3 are groups of mice injected with 0.3 µg, 1.0 µg and 3.0 µg per mouse of the conjugate vaccine, respectively. G4 represents mice that were injected with 1.0 µg of the serotype 14 polysaccharide alone. G5 and G6 are groups of mice injected with 1.0 and 3.0 µg pseudopneumolysin alone, respectively. G7 is the group of mice injected with 1.0 µg of the serotype 14 polysaccharide-pseudopneumolysin conjugate vaccine without adjuvant.

Little or no antibody responses against the polysaccharide were observed in mice of G4, G5, and G6.

Example 6

Construction of Expression Vectors for Pseudopneumolysin, Pneumococcal Autolysin, and Pneumococcal Surface Protein DNA Vaccines A. pVAX1 Vector for the Construction of a DNA Vaccine pVAX1 vector (Invitrogen) was specifically designed for use in the development of DNA vaccines. Its construction is consistent with the Food and Drug Administration's document, "Points to Consider on Plasmid DNA Vaccines for Preventive Infectious Disease Indications" published on Dec. 22, 1996.

B. Cloning and Expression of Pseudopneumolysin

PCR was carried out using Ready-to-go PCR beads (Amersham Pharmacia Biotech Inc. Piscataway, N.J.) containing primers and template pneumococcal 19A chromosomal DNA. PCR was performed as follows: 94° C., 4 minutes for 1 cycle; 94° C., 1 minute; 55° C., 1 minute; 72° C., 1.5 minutes for 30 cycles; and 72° C., 10 minutes for 1 cycle.

The amplified PCR product was digested with restriction enzymes and ligated into sites of the pVAX1 vector to generate pSA-8, pSA-45, pSA-12, pSA-42, and pSA-41. The recombinant DNA was introduced into E. coli DH5α cells by transformation and checked by digestion with restriction enzymes. The inserted gene was analyzed by DNA sequencing. In vitro transcription and translation were carried out with TnT kit according to the manufacture's protocol (Promega, Madison, Wis.) to confirm the expression of the inserted gene.

The pSA-8 expression vector encodes a polypeptide consisting of amino acids 1-460 of the pneumolysin protein of SEQ ID NO:1. The insert was generated as described above using LSYN-15 primer (5'-GACTGCTAGCCACCATG-GCAAATAAAGCAGTAAATGAC-3'; SEQ ID NO:4) and LSYN-4 primer (5'-GACTGGATCCTTACTAGAGAGT-TGTTCCCCAAATAG-3'; SEQ ID NO:5) to amplify the 1380 base pair DNA. The 1380 base pair PCR product was then restricted with NheI and BamHI and ligated into NheI and BamHI sites of pVAX1 vector to generate pSA-8.

The pSA-45 expression vector encodes a polypeptide consisting of amino acids 1-464 of the pneumolysin protein of SEQ ID NO:1. The insert was generated using LSYN-15 (5'-GACTGCTAGCCACCATGGCAAATAAAG-CAGTAAATGAC-3'; SEQ ID NO:4) and LSYN-105 (GACTGGATCCCTATACCTGAGGATAGAGAGTTG; SEQ ID NO:26) to amplify the 1392 base pair PCR product, was then restricted with NheI and BamHI and ligated into NheI and BamHI sites of pVAX1 vector to generate pSA-45.

The pSA-12 expression vector encodes a polypeptide consisting of amino acids 1-466 of the pneumolysin protein of SEQ ID NO:1. The insert was generated as described above using LSYN-15 primer (5'-GACTGCTAGCCACCATG-GCAAATAAAGCAGTAAATGAC-3'; SEQ ID NO:4) and LSYN-17 primer (5'-GACTGGATCCTTACTAATCTTC-TACCTGAGGATAG-3'; SEQ ID NO:6) to amplify the 1398 base pair DNA. The 1398 base pair PCR product was then restricted with NheI and BamHI and ligated into NheI and BamHI sites of pVAX1 vector to generate pSA-12.

The pSA-42 expression vector encodes a polypeptide consisting of amino acids 1-469 of the pneumolysin protein of SEQ ID NO:1. The insert was generated as described above using LSYN-15 primer (5'-GACTGCTAGCCACCATG-GCAAATAAAGCAGTAAATGAC-3'; SEQ ID NO:4) and LSYN-37 primer (5'-GACTGGATCCTTACTATTCTACCT-TATCTTCTACCTGAG-3'; SEQ ID NO:7) to amplify the 1407 base pair DNA. The 1407 base pair PCR product was then restricted with NheI and BamHI and ligated into NheI and BamHI sites of pVAX1 vector to generate pSA-42.

The pSA-41 expression vector encodes a polypeptide consisting of amino acids 1-470 of the pneumolysin protein of SEQ ID NO:1. The insert was generated as described above using LSYN-15 primer (5'-GACTGCTAGCCACCATG-GCAAATAAAGCAGTAAATGAC-3'; SEQ ID NO:4) and LSYN-38 primer (5'-GACTGGATCCTTACTAATTTTC-TACCTTATCTTCTACCTGAG-3'; SEQ ID NO:8) to amplify the 1410 base pair DNA. The 1410 base pair PCR product was then restricted with NheI and BamHI and ligated into NheI and BamHI sites of pVAX1 vector to generate pSA-41.

Nucleic acids containing the unmethylated cytosine-guanine ("CpG") dinucleotide in a particular sequence context or motif can be potent stimulators of several types of immune cells in vitro. Synthetic oligonucleotides containing CpG motifs can directly activate the innate immune system by stimulating B-cells to proliferate and secrete immunoglobulin, IL-6 and IL-10, NK cells to produce IFN-γ, and monocytes and dendritic cells to produce IL-6, IL-12, IL-18 TNT-α and IFN-α. A DNA motif consisting of an unmethylated CpG dinucleotide flanked by two 5' purines and two 3' pyrimidines stimulates B cells to produce IL-6 and IL-12, and stimulates CD4+T cells to produce IL-6 and IFN-gamma.

Structure-function analysis of pneumolysin has demonstrated that a domain (located at amino acids 427 to 437) at the C terminus of the polypeptide, which includes a cysteine residue, is critical for cytotoxicity. This cysteine motif is highly conserved among other members of the thiol-activated cytolysin family. Several single amino acid substitutions within this domain reduce the cytotoxicity of pneumolysin significantly. The following nucleic acid construct substitutes the cysteine motif with a CpG motif by introducing GAGCGTT at nucleotide position of 1272 and 1274 of pneumolysin (via site directed mutagenesis). The mutated nucleic acid containing the GAGCGTT immunostimulatory sequence is as follows:

```
                                            (SEQ ID NO:9)
ATGGCAAATAAAGCAGTAAATGACTTTATACTAGCTATGAATTACGATAA

AAAGAAACTCTTGACCCATCAGGGAGAAAGTATTGAAAATCGTTTCATCA

AAGAGGGTAATCAGCTACCCGATGAGTTTGTTGTTATCGAAAGAAAGAAG

CGGAGCTTGTCGACAAATACAAGTGATATTTCTGTAACAGCTACCAACGA

CAGTCGCCTCTATCCTGGAGCACTTCTCGTAGTGGATGAGACCTTGTTAG

AGAATAATCCCACTCTTCTTGCGGTCGATCGTGCTCCGATGACTTATAGT

ATTGATTTGCCTGGTTTGGCAAGTAGCGATAGCTTTCTCCAAGTGGAAGA

CCCCAGCAATTCAAGTGTTCGCGGAGCGGTAAACGATTTGTTGGCTAAGT

GGCATCAAGATTATGGTCAGGTCAATAATGTCCCAGCTAGAATGCAGTAT

GAAAAAATCACGGCTCACAGCATGGAACAACTCAAGGTCAAGTTTGGTTC

TGACTTTGAAAAGACAGGGAATTCTCTTGATATTGATTTTAACTCTGTCC

ATTCAGGCGAAAAGCAGATTCAGATTGTTAATTTTAAGCAGATTTATTAT

ACAGTCAGCGTAGATGCTGTTAAAAATCCAGGAGATGTGTTTCAAGATAC
```

-continued

```
TGTAACGGTAGAGGATTTAAAACAGAGAGGAATTTCTGCAGAGCGTCCTT

TGGTCTATATTTCGAGTGTTGCTTATGGGCGCCAAGTCTATCTCAAGTTG

GAAACCACGAGTAAGAGTGATGAAGTAGAGGCTGCTTTTGAAGCTTTGAT

AAAAGGAGTCAAGGTAGCTCCTCAGACAGAGTGGAAACAGATTTTGGACA

ATACAGAAGTGAAGGCGGTTATTTTAGGGGGCGACCCAAGTTCGGGTGCC

CGAGTTGTAACAGGCAAGGTGGATATGGTAGAGGACTTGATTCAAGAAGG

CAGTCGCTTTACAGCAGATCATCCAGGCTTGCCGATTTCCTATACAACTT

CTTTTTTACGTGACAATGTAGTTGCGACCTTTCAAAATAGTACAGACTAT

GTTGAGACTAAGGTTACAGCTTACAGAAACGGAGATTTACTGCTGGATCA

TAGTGGTGCCTATGTTGCCCAATATTATATTACTTGGAATGAATTATCCT

ATGATCATCAAGGTAAGGAAGTCTTGACTCCTAAGGCTTGGGACAGAAAT

GGGCAGGATTTAACGGCTCACTTTACCACTAGTATTCCTTTAAAAGGGAA

TGTTCGTAATCTCTCTGTCAAAATTAGAGAGCGTTCCGGGCTTGCCTGGG

AATGGTGGCGTACGGTTTATGAAAAAACCGATTTGCCACTAGTGCGTAAG

CGGACGATTTCTATTTGGGGAACAACTCTCTATCCTCAGGTAGAAGATAA

GGTAGAAAATGAC.
```

In another embodiment, the immunostimulatory DNA sequence GAGCGTT was introduced (via site directed mutagenesis) at nucleotide position 1272 to 1274 of a pseudopneumolysin having 33 nucleotides deleted at the C-terminal. The pseudopneumolysin DNA with the immunostimulatory sequence is as follows:

```
                                             (SEQ ID NO:10)
ATGGCAAATAAAGCAGTAAATGACTTTATACTAGCTATGAATTACGATAA

AAAGAAACTCTTGACCCATCAGGGAGAAAGTATTGAAAATCGTTTCATCA

AAGAGGGTAATCAGCTACCCGATGAGTTTGTTGTTATCGAAAGAAAGAAG

CGGAGCTTGTCGACAAATACAAGTGATATTTCTGTAACAGCTACCAACGA

CAGTCGCCTCTATCCTGGAGCACTTCTCGTAGTGGATGAGACCTTGTTAG

AGAATAATCCCACTCTTCTTGCGGTCGATCGTGCTCCGATGACTTATAGT

ATTGATTTGCCTGGTTTGGCAAGTAGCGATAGCTTTCTCCAAGTGGAAGA

CCCCAGCAATTCAAGTGTTCGCGGAGCGGTAAACGATTTGTTGGCTAAGT

GGCATCAAGATTATGGTCAGGTCAATAATGTCCCAGCTAGAATGCAGTAT

GAAAAAATCACGGCTCACAGCATGGAACAACTCAAGGTCAAGTTTGGTTC

TGACTTTGAAAAGACAGGGAATTCTCTTGATATTGATTTTAACTCTGTCC

ATTCAGGCGAAAAGCAGATTCAGATTGTTAATTTTAAGCAGATTTATTAT

ACAGTCAGCGTAGATGCTGTTAAAAATCCAGGAGATGTGTTTCAAGATAC

TGTAACGGTAGAGGATTTAAAACAGAGAGGAATTTCTGCAGAGCGTCCTT

TGGTCTATATTTCGAGTGTTGCTTATGGGCGCCAAGTCTATCTCAAGTTG

GAAACCACGAGTAAGAGTGATGAAGTAGAGGCTGCTTTTGAAGCTTTGAT

AAAAGGAGTCAAGGTAGCTCCTCAGACAGAGTGGAAACAGATTTTGGACA

ATACAGAAGTGAAGGCGGTTATTTTAGGGGGCGACCCAAGTTCGGGTGCC

CGAGTTGTAACAGGCAAGGTGGATATGGTAGAGGACTTGATTCAAGAAGG
```

-continued

```
CAGTCGCTTTACAGCAGATCATCCAGGCTTGCCGATTTCCTATACAACTT

CTTTTTTACGTGACAATGTAGTTGCGACCTTTCAAAATAGTACAGACTAT

GTTGAGACTAAGGTTACAGCTTACAGAAACGGAGATTTACTGCTGGATCA

TAGTGGTGCCTATGTTGCCCATATTATATACTTGGAATGAATTATCCTAT

GATCATCAAGGTAAGGAAGTCTTGACTCCTAAGGCTTGGGACAGAAATGG

GCAGGATTTAACGGCTCACTTTACCACTAGTATTCCTTTAAAAGGGAATG

TTCGTAATCTCTCTGTCAAAATTAGAGAGCGTTCCGGGCTTGCCTGGGAA

TGGTGGCGTACGGTTTATGAAAAAACCGATTTGCCACTAGTGCGTAAGCG

GACGATTTCTATTTGGGGAACAACTCTC.
```

D. Cloning and Expression of Pneumococcal Autolysin Gene

The pSA-59 expression vector encodes a 316 amino acid autolysin (Aly) polypeptide. The Type 19A Aly gene was amplified by PCR using Ready-to-go PCR beads containing primers and template from pneumococcal 19A chromosomal DNA. PCR was performed as follows: 94° C., 4 minutes for 1 cycle; 94° C., 1 minute; 50° C., 1 minute; 72° C., 1 minute, 15 seconds for 30 cycles; and 72° C., 10 minutes for 1 cycle. The insert was generated using LSYN-74 primer (5' -GACTAAGCTTGCCACCATGGAAATTAATGTGAGTAAATTAAG-3'; SEQ ID NO:11) and LSYN-89 primer (5'-CTGACTCGAGTTATTTTACTGTAATCAAGCCATC-3'; SEQ ID NO:12) to amplify the 948 base pair DNA.

PCR-synthesized DNA was digested with HindIII and XhoI and ligated at HindIII and XhoI sites of pVAX1 to generate pSA-59 (Aly). The recombinant DNA was introduced into *E. coli* DH5α cells by transformation checked by digestion with restriction enzymes, HindIII and XhoI. The Aly insert were confirmed by DNA sequencing. In vitro transcription and translation was carried out with TnT kit (Promega, Madison, Wis.) according to manufacture's protocol to confirm the expression of pSA-59.

The nucleic acid sequence of the pSA-59 Aly insert is as follows:

```
                                             (SEQ ID NO:13)
ATGGAAATTAATGTGAGTAAATTAAGAACAGATTTGCCTCAAGTTGGCGT

GCAACCATATAGGCAAGTACACGCACACTCAACTGGGAATCCGCATTCAA

CCGTACAGAATGAAGCGGATTATCATTGGCGGAAAGACCCAGAATTAGGT

TTTTTCTCGCACATTGTTGGGAACGGATGCATCATGCAGGTAGGACCTGT

TAATAATGGTGCCTGGGACGTTGGGGGCGGTTGGAATGCTGAGACCTATG

CAGCGGTTGAACTGATTGAAAGCCATTCAACTAAAGAAGAGTTCATGACG

GACTACCGCCTTTATATCGAACTCTTACGCAATCTAGCAGATGAAGCAGG

TTTGCCGAAAACGCTTGATACAGGGAGTTTAGCTGGAATTAAAACGCACG

AGTATTGCACGAATAACCAACCAAACAACCACTCAGACCATGTGGATCCA

TACCCTTACTTGGCAAAATGGGGCATTAGCCGTGAGCAGTTTAAGCATGA

TATTGAGAACGGCTTGACGATTGAAACAGGCTGGCAGAAGAATGACACTG

GCTACTGGTACGTACATTCAGACGGCTCTTATCCAAAAGACAAGTTTGAG

AAAATCAATGGCACTTGGTACTACTTTGACAGTTCAGGCTATATGCTTGC
```

-continued

```
AGACCGCTGGAGGAAGCACACAGACGGCAATTGGTACTACTTTGACCAAT

CAGGCGAAATGGCTACAGGCTGGAAGAAAATCGCTGAGAAGTGGTACTAT

TTCAACGAAGAAGGTGCCATGAAGACAGGCTGGGTCAAGTACAAGGACAC

TTGGTACTACTTAGACGCTAAAGAAGGCGCAATGGTATCAAATGCCTTTA

TCCAGTCAGCGGACGGAACAGGCTGGTACTACCTCAAACCAGACGGAACA

CTGGCAGACAAGCCAGAATTCACAGTAGAGCCAGATGGCTTGATTACAGT

AAAA.
```

The amino acid sequence encoded by the pSA-59 Aly insert is as follows:

```
                                            (SEQ ID NO:14)
MEINVSKLRTDLPQVGVQPYRQVHAHSTGNPHSTVQNEADYHWRKDPELG

FFSHIVGNGCIMQVGPVNNGAWDVGGGWNAETYAAVELIESHSTKEEFMT

DYRLYIELLRNLADEAGLPKTLDTGSLAGIKTHEYCTNNQPNNHSDHVDP

YPYLAKWGISREQFKHDIENGLTIETGWQKNDTGYWYVHSDGSYPKDKFE

KINGTWYYFDSSGYMLADRWRKHTDGNWYYEDQSGEMATGWKKIAEKWYY

FNEEGAMKTGWVKYKDTWYYLDAKEGAMVSNAFIQSADGTGWYYLKPDGT

LADKPEFTVEPDGLITVK.
```

E. Cloning and Expression of N-terminal Pneumococcal Surface Protein A (PspA) Gene The pSA-60 expression vector encodes a 459 amino acid PspA polypeptide. The type 19A PspA gene was amplified by PCR using Ready-to-go PCR beads containing primers and template from pneumococcal 19A chromosomal DNA. PCR was performed as follows: 94° C., 4 minutes for 1 cycle; 94° C., 1 minute; 50° C., 1 minute; 72° C., 1 minute, 15 seconds for 30 cycles; and 72° C., 10 minute for 1 cycle. The insert was generated using LSYN-90 (5'-GACTAAGCTTGCCAC-CATGGAA GAAGCTCCCGTAGCTAGTCAG-3'; SEQ ID NO:15) with LSYN-78 primer (5'-GACTCTCGAGCTATC-CATCAGGGCCTAACTCATTAAG-3'; SEQ ID NO:16) to amplify the 1377 base pair DNA. PCR-synthesized DNA was digested with HindIII and XhoI and ligated at HindIII and XhoI sites of pVAX1 to generate pSA-60 (PspA). The recombinant DNA was introduced into *E. coli* DH5α cells by transformation checked by digestion with restriction enzymes, HindIII and XhoI. The PspA insert was confirmed by DNA sequencing. In vitro transcription and translation was carried out with TnT kit (Promega, Madison, Wis.) according to manufacture's protocol to confirm the expression of pSA-60.

The nucleic acid sequence of the pSA-60 PspA insert is as follows:

```
                                            (SEQ ID NO:17)
ATGGAAGAAGCTCCCGTAGCTAGTCAGTCTAAAGCTGAGAAAGACTATGA

TGCAGCAGTGAAAAAATCTGAAGCTGCTAAGAAGGCTTACGAAGAAGCTA

AAAAGAAAGCAGAAGACGCTCAGAAAAAATATGATGAGGATCAGAAGAAA

ACTGAGGCAAAAGCGGATAAGGAAGCAAAAGCATCTGCGGAAATAGATAA

AGCCACGTTTGCTGTACAAAGTGCGTATGTAAAATTTTTAAATGTCCAAT

CTAATCGTCAAATTTCGGAGAATGAACGAAAAAAACAATTAGCAGAAATA

GATAAAGAGATAGAGAATGCTAAACAAAATTTACAGAATAAACAGGAAGA

ATTTAATAAGGTTAGAGCAGAAGTAATTCCTGAAGCAAAGGGGTTAGCTG

TTACTAAACAAAAAGCGGAAGAAGCTAAAAAAGAAGCAGAAGTAGCTAAG

AGAAAATATGATTATGCAACTCTAAAGGTAGCACTAGCGAAGAAAGAAGT

AGAGGCTAAGGAACTTGAAATTGAAAAACTTCAATATGAAATTTCTACTT

TGGAACAAGAAGTTGCTATTTGCTCAACATCAAGTAGATAATTTGAAAAA

ACTTCTTGCTGGTGCGGATCCTGATGATGGCACAAAAGTTATAGAAGCTA

AATTAAACAAAGGAGAAGCTGAGCTAAACGCTAAACAAGCTGAGTTAGCA

AAAAAACAAACAGAACTTGAAAAACTTCTTGACAGCCTTGATCCTGAAGG

TAAGACTCAGGATGAATTAGATAAAGAAGCTGCTGAAGCTGAGTTGGATA

AAAAAGCTGATGAACTTCAAAATAAAGTTGCTGATTTAGAAAAAGGAATT

GCTCCTTATCAAATCAAAGTCGCTGAAFFAAATAAAGAAATTGCTAGACT

TCAAAGCGATTTAAAAGATGCTGAAGAAAATAATGTAGAAGACTATATTA

AAGAAGGTTTAGAGCAAGCTATCGCTGATAAAAAAGCTGAATTAGCTACA

ACTCAACAAAACATAGATAAAACTCAAAAAGATTTAGAGGATGCTGAATT

AGAACTTGAAAAAGTATTAGCTACATTAGACCCTGAAGGTAAAACTCAAG

ATGAATTAGATAAAGAAGCTGCAGAAGATGCTAATATTGAAGCTCTTCAA

AACAAAGTTGCTGATCTAGAAAACAAGGTTGCTGAATTAGATAAAGAAGT

TACTAGACTTCAAAGCGATTTAAAAGATGCTGAAGAAAACAATGTAGAAG

ACTACGTFAAAGAAGGCTTAGATAAAGCTCTTACTGATAAAAAAGTTGAA

TTAAATAATACTCAAAAAGCATTAGATACTGCTCAAAAAGCATTAGATAC

TGCTCTTAATGAGTTAGGCCCTGATGGA.
```

The amino acid sequence encoded by the pSA-60 PspA insert is as follows:

```
                                            (SEQ ID NO:18)
MEEAPVASQSKAEKDYDAAVKKSEAAKKAYEEAKKKAEDAQKKYDEDQKK

TEAKADKEAKASAEIDKATFAVQSAYVKFLNVQSNRQISENERKKQLAEI

DKEIENAKQNLQNKQEEFNKVRAEVIPEAKGLAVTKQKAEEAKKEAEVAK

RKYDYATLKVALAKKEVEAKELEIEKLQYEISTLEQEVAIAQHQVDNLKK

LLAGADPDDGTKVIEAKLNKGEAELNAKQAFLAKKQTELEKLLDSLDPEG

KTQDELDKEAAEAELDKKADELQNKVADLEKGIAPYQIKVAELNKEIARL

QSDLKDAEENNVEDYIKEGLEQAIADKKAELATTQQNIDKTQKDLEDAEL

ELEKVLATLDPEGKTQDELDKEAAEDANIEALQNKVADLENKVAELDKEV

TRLQSDLKDAEENNVEDYVKEGLDKALTDKKVELNNTQKALDTAQKALDT

ALNELGPDG.
```

Example 7

Immunogenicity of DNA Vaccines

Plasmid vector pSA-7 encodes a full length pneumolysin protein. Type 19A Ply gene was amplified by PCR using Ready-to-go PCR beads containing primers and template from Pneumococcal 19A chromosomal DNA. PCR was performed at 94° C. 4 min for 1 cycle, 94° C. 1 min, 55° C. 1 min, and 72° C. 1.5 min for 30 cycles, and 72° C. 10 min for 1 cycle. LSYN-15 primer (5'-GACTGCTAGCCACCATG-GCAAATAAAGCAGTAAATGAC-3'; SEQ ID NO:4) complementary to Ply nucleotides 1 to 24 at 5' end was used with LSYN-3 primer (5'-CAGTGGATCCTTACTAGT-CATTTTCTACCTTATC-3'; SEQ ID NO:3) complementary to Ply nucleotides 1396 to 1413 at 3' end to amplify the 1413 base pair DNA encoding the 471 amino acid full-length, wild type Ply protein. The PCR-synthesized DNA fragment was treated with NheI and BamHI and ligated into NheI and BamHI sites of pVAX1 expression vector to generate pSA-7. The recombinant DNA was introduced into *E. coli* DE5α cells by transformation and checked by digestion with restriction enzymes, NheI and BamHI. The inserted type 19A wild type Ply gene was confirmed by DNA sequencing.

Plasmid vector pSA-10 encodes a C-terminal truncated pneumolysin protein (lacking 114 amino acids at the C-terminus of Ply). Type 19A Ply gene was amplified by PCR using Ready-to-go PCR beads containing primers and template from Pneumococcal 19A chromosomal DNA. PCR was performed at 94° C. 4 min for 1 cycle, 94° C. 1 min, 55° C. 1 min, and 72° C. 1.5 min for 30 cycles, and 72° C. 10 min for 1 cycle. LSYN-15 primer (5'-GACTGCTAGCCACCATG-GCAAATAAAGCAGTAAATGAC-3'; SEQ ID NO:4) complementary to Ply nucleotides 1 to 24 at 5' end was used with LSYN-6 primer (5'-CTGAGGATCCTTACTAAGCTG-TAACCTTAGTCTC-3'; SEQ ID NO:19) complementary to Ply nucleotides 1054 to 1071 at the 3' end to amplify a 1071 base pair DNA encoding a 357 amino acid polypeptide. The PCR-synthesized DNA fragment was treated with NheI and BamHI and ligated into NheI and BamHI sites of pVAX1 expression vector to generate pSA-10. The recombinant DNA was introduced into *E. coli* DE5α cells by transformation and checked by digestion with restriction enzymes, NheI and BamHI. The inserted type 19A pseudopneumolysin gene was confirmed by DNA sequencing.

Plasmid vector pSA-26 encodes a full length pneumolysin carrying a CpG motif. PCR Primers LSYN-34 and LSYN-33, containing two complementary oligonucleotides carrying CpG motif at the 3' termini, were used to prime PCR1 and PCR2. The second primers LSYN-15 and LSYN-3 are complementary to sequences lying N and C-terminal of pneumolysin, respectively. In separate amplification, the first PCR products, PCR1 (1.2 kb) and PCR2 (150 bp) were generated by PCR using Ready-to-go PCR beads containing primers LSYN-15 and -34 (PCR1) and LSYN-33 and -3 (PCR2) and template pSA7 containing full-length pneumolysin gene. The first PCR products were mixed and denatured and used as templates to generate second PCR product, which was primed by the second set primers LSYN-15 and -3. The second PCR product was cut with NheI and BamHI, and cloned at NheI and BamHI of pVAX1 to generate pSA-26. PCR was performed at 94° C. 4 min for 1 cycle, 94° C. 1 min, 55° C. 1 min, and 72° C. 1 min for 30 cycles, and 72° C. 8 min for 1 cycle.

The sequence of primers LSYN-3, LSYN-15, LSYN-33 and LSYN-34 are as follows:

```
LSYN-3 primer
(5'-CAGTGGATCCTTACTAGTCATTTTCTACCTTATC-3';
SEQ ID NO:3);

LSYN-15 primer
(5'-GACTGCTAGCCACCATGGCAAATAAAGCAGTAAATGAC-3';
SEQ ID NO:4);
```

```
-continued
LSYN-33 primer
(5'-CAAAATTAGAGAACGTTCCGGGCTTGCCTGGGAATGG-3';
SEQ ID NO:20), LSYN-34 primer
(5'-GCCCGGAACGTTCTCTAATTTTGACAGAGAGATTACG-3';
SEQ ID NO:21).
```

The recombinant DNA was introduced into *E. coli* DE5α cells by transformation and checked by digestion with restriction enzymes, NheI and BamHI. The inserted type 19A wild type Ply gene carrying a CpG motif was confirmed by DNA sequencing.

Plasmid vector pSA-27 contains a CpG motif and encodes a C-terminal truncation of pneumolysin (11 amino acids deleted). Primers LSYN-34 and LSYN-33, containing two complementary oligonucleotides carrying CpG motif at the 3' termini, were used to prime PCR1 and PCR2. The second primers LSYN-15 and LSYN-3 are complementary to sequences lying N and C-terminal of pneumolysin, respectively. In separate amplification, the first PCR products, PCR1 (1.2 kb) and PCR2 (150 bp) were generated by PCR using Ready-to-go PCR beads containing primers LSYN-15 and -34 (PCR1) and LSYN-33 and -3 (PCR2) and template pSA-7 containing full-length pneumolysin gene.

The first PCR products were mixed and denatured and used as templates to generate a second PCR product, which was primed by the second set primers LSYN-15 and -4. The second PCR product was cut with NheI and BamHI, and cloned at NheI and BamHI of pVAX1 to generate pSA-27. PCR was performed at 94° C. 4 min for 1 cycle, 94° C. 1 min, 55° C. 1 min, and 72° C. 1 min for 30 cycles, and 72° C. 8 min for 1 cycle. The oligonucleotides of primers LSYN-3, LSYN-4, LSYN-15, LSYN-33 and LSYN-34 are as follows: LSYN-3 primer (5'-CAGTGGATCCTTACTAGT-CATTTTCTACCTTATC-3'; SEQ ID NO:3); LSYN-4 primer (5'-GACTGGATCCTTACTAGAGAGTTGTTC-CCCAAATAG-3'; SEQ ID NO:5) LSYN-15 primer

```
LSYN-15 primer
(5'-GACTGCTAGCCACCATGGCAAATAAAGCAGTAAATGAC-3';
SEQ ID NO:4);

LSYN-33 primer
(5'-CAAAATTAGAGAACGTTCCGGGCTTGCCTGGGAATGG-3';
SEQ ID NO:20);

LSYN-34 primer
(5'-GCCCGGAACGTTCTCTAATTTTGACAGAGAGATTACG-3';
SEQ ID NO:21).
```

GCCCGGAACGTTCTCTAATTTTGACA-GAGAGATTACG-3'; SEQ ID NO:21). The recombinant DNA was introduced into *E. coli* DE5α cells by transformation and checked by digestion with restriction enzymes, NheI and BamHI. The inserted type 19A pseudopneumolysin gene carrying CpG motif was confirmed by DNA sequencing.

A vaccination program which entails priming with a DNA vector and boosting with a protein has resulted in the generation of a high level of specific immunity and, in some cases, afforded protection against infectious agents that currently pose great problems for vaccine development. In these experiments, rabbits were primed three times with a pneumolysin DNA vector and boosted with a pneumolysin protein without adjuvant.

Figure 16:
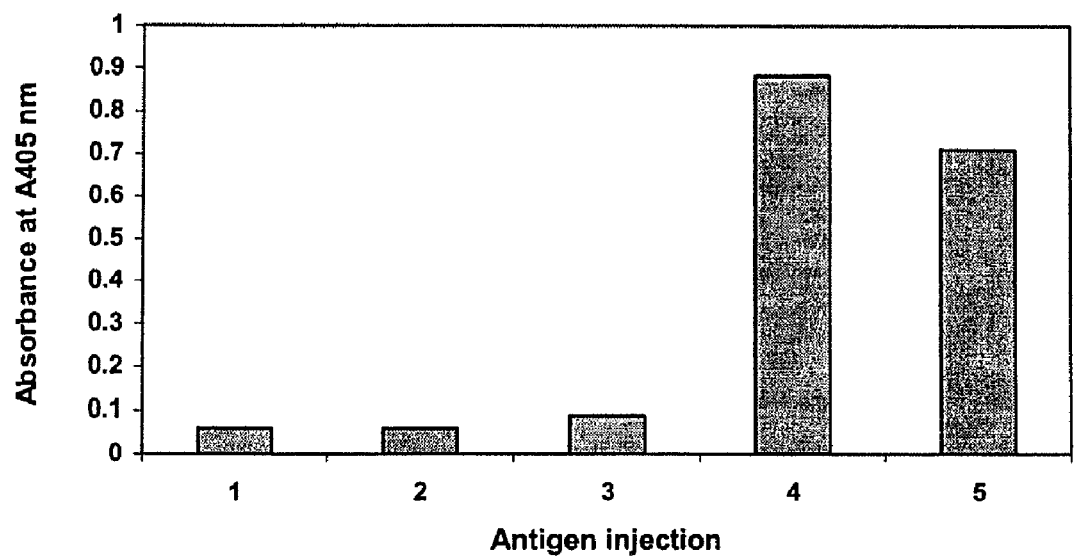
FIG. 16 is a graph depicting the antibody response in rabbit against pneumolysin using a prime-boost strategy for pseudopneumolysin DNA vaccination.

FIG. 16 is a graph depicting an anti-pneumolysin antibody response in rabbits using a prime-boost strategy for pseudopneumolysin DNA vaccination, as described above. Lanes 1, 2, and 3 represent immune responses 7 days after a first (1), second (2), and third (3) intramuscular pseudopneumolysin DNA vaccination. Lane 4 represents the response 10 days after protein boost (200 μg pneumolysin). Lane 5 depicts the antibody response 10 days after injection of 200 μg pneumolysin protein together with TiterMax adjuvant. The results demonstrate that three injections of DNA plus a boost with protein can result in a higher antibody response compared to a traditional protein vaccination method using an adjuvant.

DNA vaccines pSA-59, and pSA-60, and one vector control plasmid DNA, in the amount of 100 μg each in a total volume of 0.1 mL in 1×PBS, were each injected intramuscularly into both quadriceps muscle or hind limbs of Balb/C mice. Mice were injected with 4 doses of 100 μg DNA vaccines with 2 week intervals between the injections. At 7 days after the final injection, the serum levels of IgG antibodies were measured by ELISA. The mice that received 4 injections DNA vaccines produced 9600 fold more IgG Ab than did the control group. These results indicate that plasmid DNA can express autolysin or pneumococcal surface protein A antigens in vivo and stimulate the immune system to produce high levels of specific IgG antibodies in mice.

Figure 17:
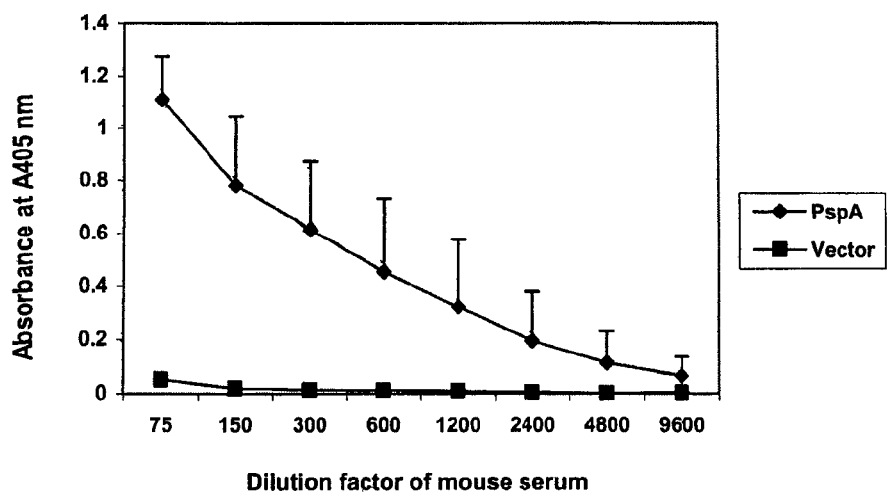
FIG. 17 is a graph depicting an antibody response after injection with an expression vector encoding pneumococcal surface protein A DNA vaccine.
Figure 18:
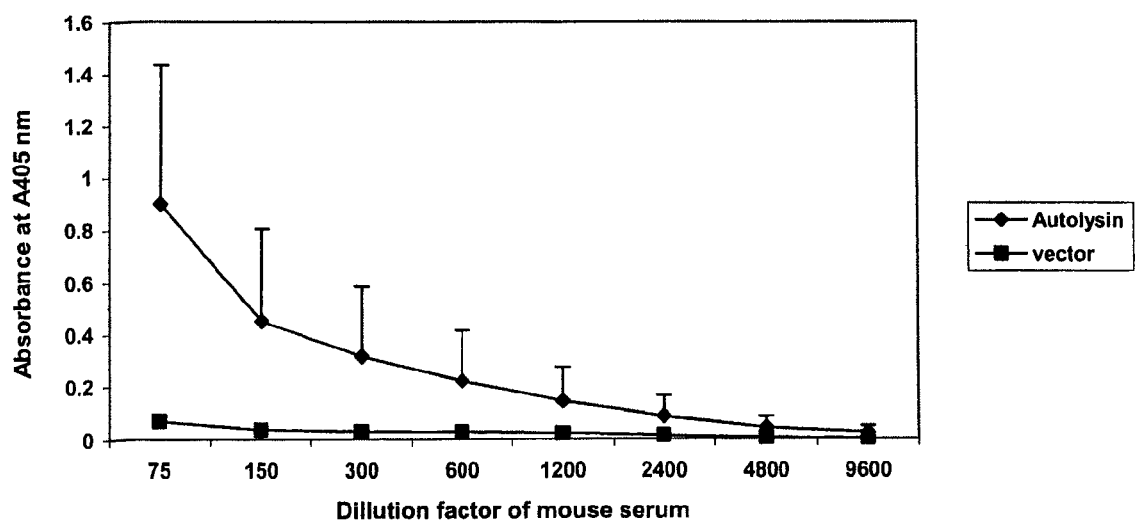
FIG. 18 is a graph depicting an antibody response after injection with an expression vector encoding autolysin DNA vaccine.

FIG. 17 is a graph of the antibody response to pneumococcal surface protein A 7 days after the fourth injection with the PspA DNA vaccine. FIG. 18 is a graph of the antibody response to pneumococcal autolysin 7 days after the fourth injection with the autolysin DNA vaccine.

Example 8

Protective Immunity and Cross-Protection Against Challenge With Heterologous Serotypes of Virulent Pneumococci Mice were injected intraperitonealy with three doses of 2.5 μg serotype 14 polysaccharide-pseudopneumolysin (-7 amino acids) conjugate at 2 week intervals. In control groups, the conjugate was substituted with PBS. Eight days after the third injections, the immunized mice were challenged intraperitonealy with $1\times10^5$ to $1\times10^6$ CFU (colony forming unit) pneumococci/0.1 mL. The exact number of CFU per milliliter injected was determined by plate count on sheep blood agar plate. At 1, 3, and 5 hours after challenge, 5 μL and 20 μL of blood samples of each mouse were plated onto sheep blood agar plate and incubated at 37° C. overnight. Significant differences were detected for bacterial clearance from blood samples of conjugate vaccinated mice relative to controls following challenge.

Figure 19:
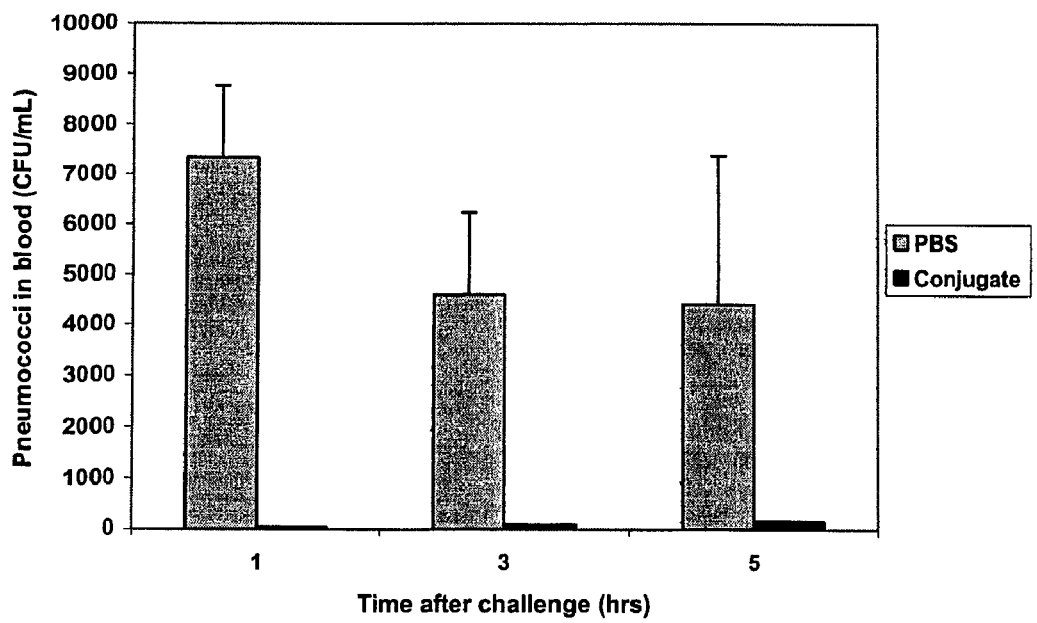
FIG. 19 is a graph depicting bacterial clearance in mice challenged with *S. pneumoniae* serotype 14 after immunization with a type 14 polysaccharide-pseudopneumolysin conjugate.

FIG. 19 shows bacterial clearance from the blood of mice immunized with a serotype 14 polysaccharide-pseudopneumolysin conjugate when challenged with type 14 pneumococci. There were significant differences ($P<0.01$) of CFUs between the conjugate and PBS treated groups 1, 3, and 5 hours after challenge.

Figure 20:
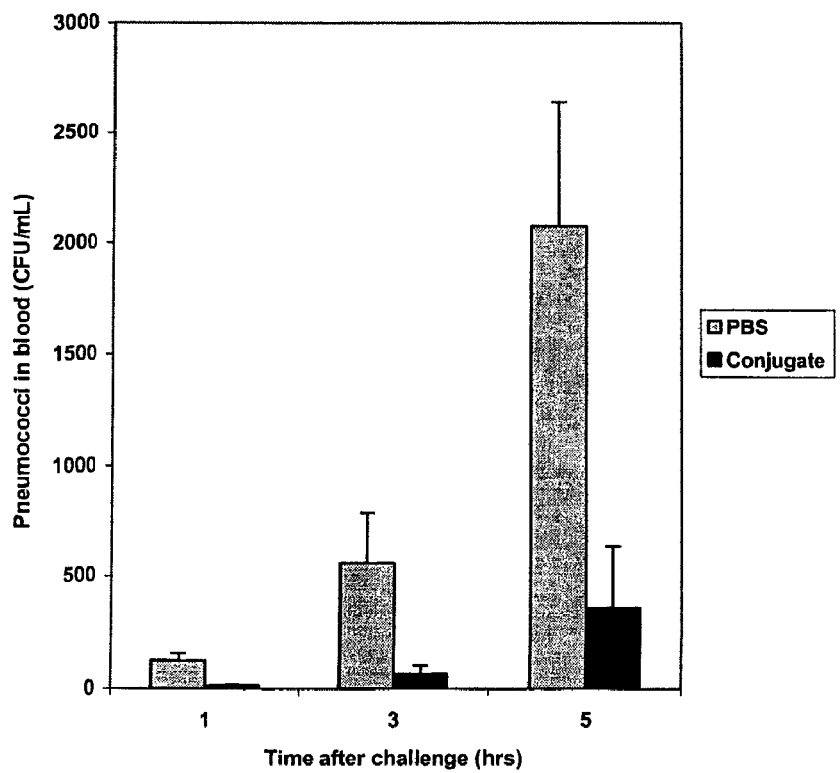
FIG. 20 is a graph depicting bacterial clearance in mice challenged with *S. pneumoniae* serotype 7 after immunization with a type 14 polysaccharide-pseudopneumolysin conjugate.

FIG. 20 shows bacterial clearance from the blood of mice immunized with a serotype 14 polysaccharide-pseudopneumolysin conjugate when challenged with type 7 pneumococci. There were significant differences ($P<0.01$) of CFUs between the conjugate and PBS treated groups at 1, 3, and 5 hours after challenge. These data also indicate that mice immunized with the conjugate were provided cross-protection against challenge with a heterologous pneumococcal serotype.

Figure 21:
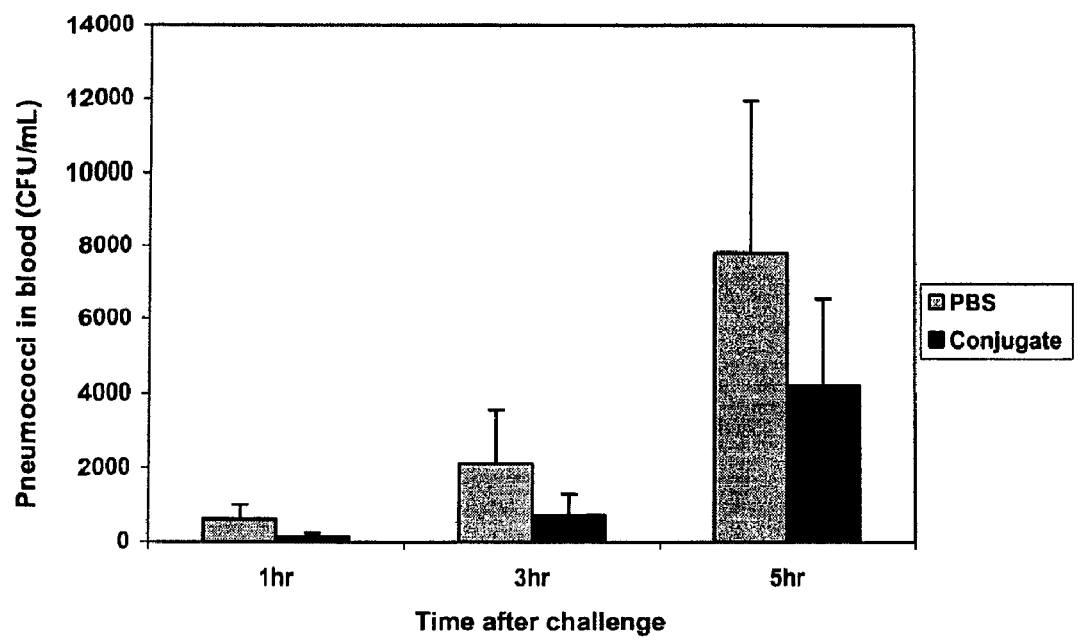
FIG. 21 is a graph depicting bacterial clearance in mice challenged with *S. pneumoniae* serotype 6B after immunization with a serotype 14 polysaccharide-pseudopneumolysin conjugate.

FIG. 21 shows bacterial clearance from the blood of mice immunized with a serotype 14 polysaccharide-pseudopneumolysin conjugate when challenged with type 6B pneumococci. There were significant differences ($P<0.05$) of CFUs between the conjugate and PBS treated groups at 1, 3, and 5 hours after challenge. These data also indicate that mice immunized with the conjugate were provided cross-protection against challenge with a heterologous pneumococcal serotype.

Figure 22:
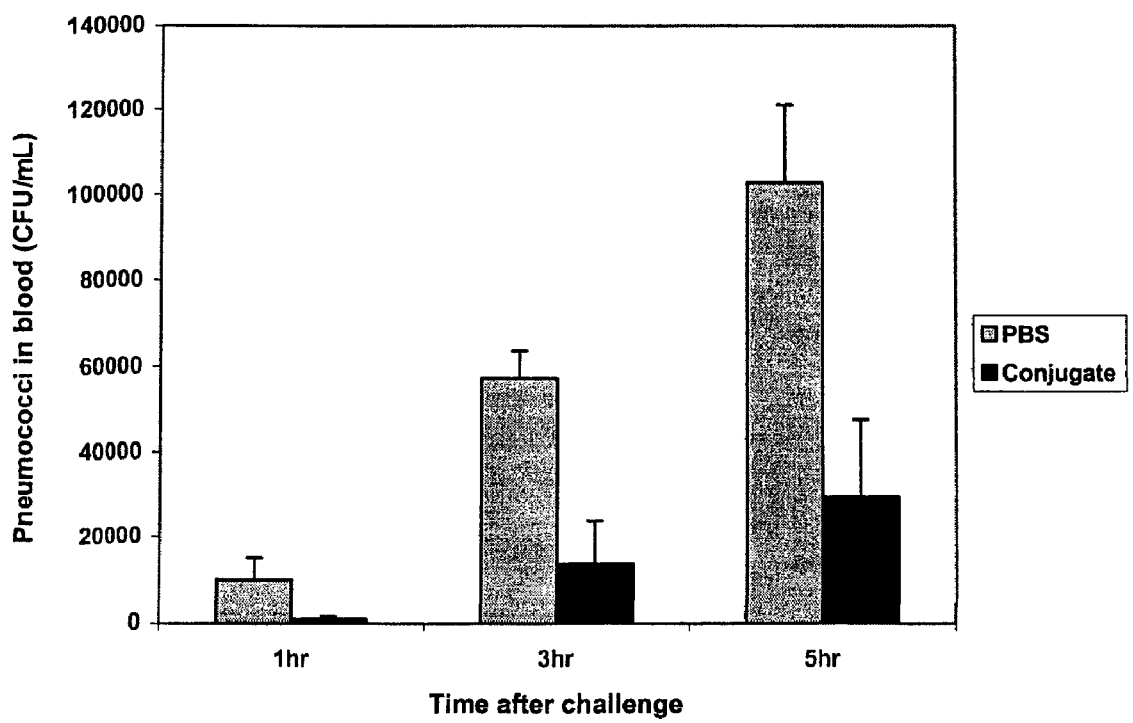
FIG. 22 is a graph depicting bacterial clearance in mice challenged with *S. pneumoniae* serotype 18C after immunization with a serotype 14 polysaccharide-pseudopneumolysin conjugate.

FIG. 22 shows bacterial clearance from the blood of mice immunized with a serotype 14 polysaccharide-pseudopneumolysin conjugate when challenged with type 18C pneumococci. There were significant differences ($P<0.01$) of CFUs between the conjugate and PBS treated groups at 1, 3, and 5 hours after challenge. These data also indicate that mice immunized with the conjugate were provided cross-protection against challenge with a heterologous pneumococcal serotype.

Figure 23:
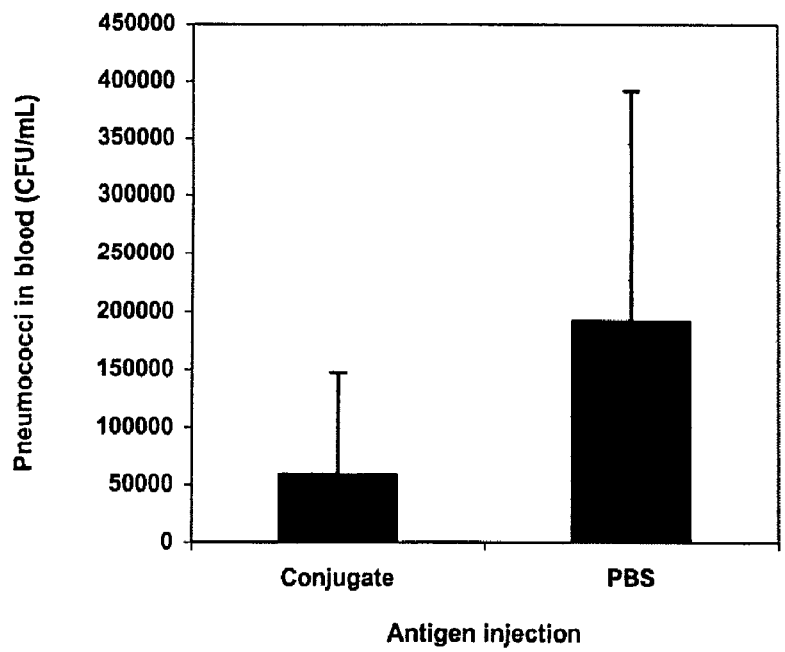
FIG. 23 is a graph depicting bacterial clearance 1 hour following challenge with *S. pneumoniae* serotype 23F after immunization with a serotype 14 polysaccharide-pseudopneumolysin conjugate.
Figure 24:
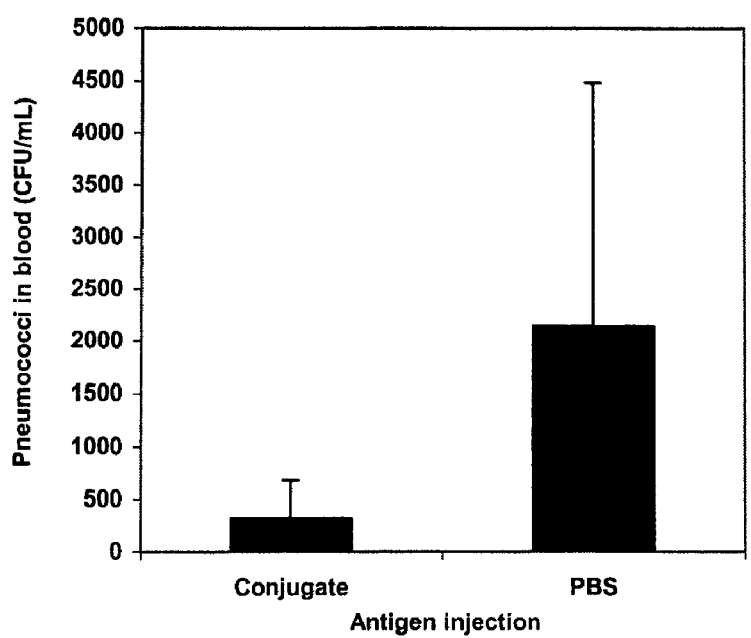
FIG. 24 is a graph depicting bacterial clearance 3 hours following challenge with *S. pneumoniae* serotype 23F after immunization with a serotype 14 polysaccharide-pseudopneumolysin conjugate.
Figure 25:
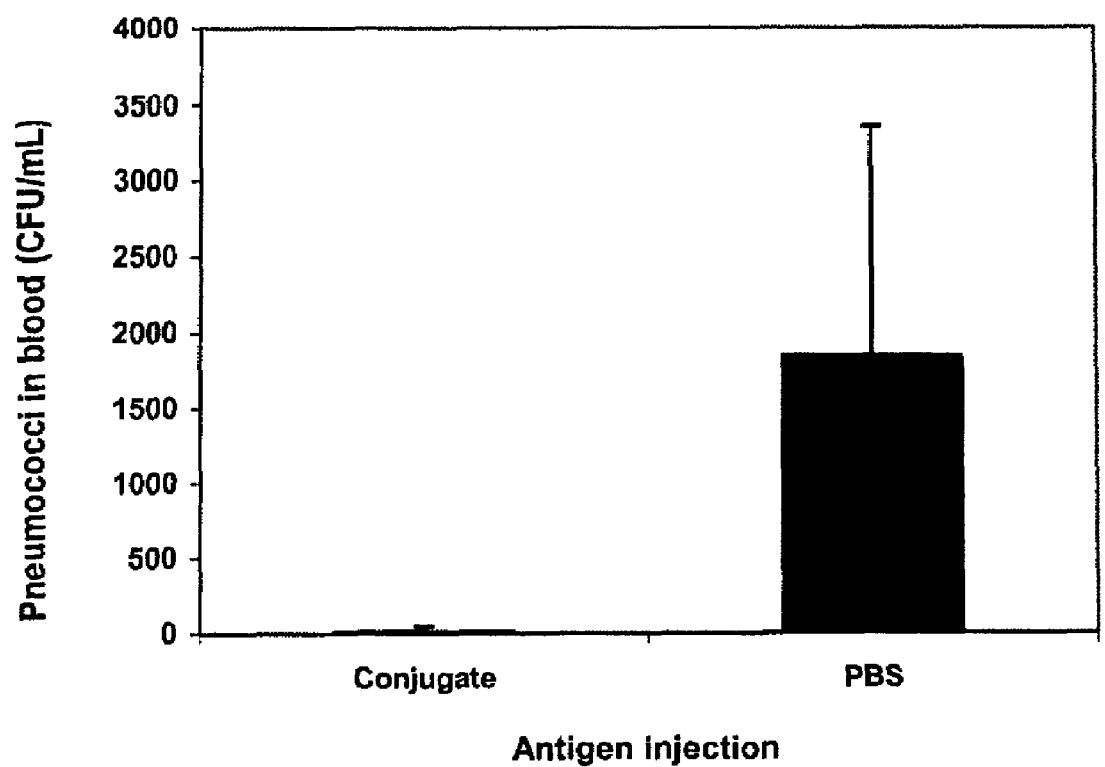
FIG. 25 is a graph depicting bacterial clearance 5 hours following challenge with *S. pneumoniae* serotype 23F after immunization with a serotype 14 polysaccharide-pseudopneumolysin conjugate.

FIGS. 23-25 show bacterial clearance from the blood of mice immunized with a serotype 14 polysaccharide-pseudopneumolysin conjugate when challenged with type 23F pneumococci. There were significant differences ($P<0.01$) of CFUs between the groups of conjugate and PBS at 1 hour (FIG. 23), 3 hours (FIG. 24) and 5 hours (FIG. 25) after challenge. These data also indicate that mice immunized with the conjugate were provided cross-protection against challenge with a heterologous pneumococcal serotype.

Example 9

Opsonophagocytic Assay

A. Opsonophagocytic Assay

The functional activity of an antibody against serotype 14 pneumococcal polysaccharide was measured by an opsonophagocytic assay using human polymorphonuclear leukocytes (PMNL). Antisera were serially diluted (two-fold) and 20 μL of each serum sample was combined with 20 μL of bacterial suspension, containing approximately 200 CFU in brain heart infusion medium and incubated at 37° C. for 15 minutes. After incubation, 10 μL of baby rabbit complement and 40 μL of PMNL ($4\times10^5$ cells) were added. The mixture was incubated at 37° C. in a 5% $CO_2$ atmosphere for 60 minutes. To obtain viable cell counts, a 20 μL aliquot from each sample was inoculated on triplicate blood agar plates and kept at 37° C. overnight. Complement control included all test reagents except antibodies to pneumococci. Opsonophagocytic titers were reported as the reciprocal of the highest serum dilution with >50% killing of bacteria compared with growth in the complement.

B. Phagocytes

Fresh PMNL were isolated from peripheral blood of a healthy adult volunteer by dextran sedimentation and ficoll (ICN Biomedical Company, #16-922-54 Lymphocyte Separation Medium) separation of mononuclear cells and PMNL. Red blood cells were lysed with ACK lysis buffer (BioFluids, Catalog number p304-100). The final concentration of cells was adjusted to $1\times10^7$ cells/mL in BME (Life Technologies GIBCO BRL, Basal Medium Eagle). 40 μL of PMNL 2-4× $10^5$ cells was used for each sample.

C. Mouse Serum and Bacteria

Mouse antisera against 14 polysaccharide were serially diluted in brain-heart infusion medium (two-fold, from 1:2 to 1:256) and 20 μL of each serum sample was mixed with 20 ul of bacterial suspension (200 CFU of *S. pneumoniae* serotype 14) at 37° C. for 15 minutes.

Serotype 14 S. pneumoniae was cultured in brain-heart infusion medium at 37° C. for 10 hours. 10 fold serial dilutions were made to determine the number of bacteria used for this experiment. 100 ul of sample was applied to a plate. 10 CFU was found on the plate using the sample with a $1:10^7$ dilution and 91 CFU was found on the plate using the sample with a $1:10^6$ dilution. Therefore, the concentration of the bacteria used for the experiment was determined to be about $1\times10^9$ CFU/mL. Serotype 14 S. pneumoniae $1\times10^9$ CFU/mL was diluted to $1\times10^4$ CFU/mL. 200 CFU/20 µL was used for each sample.

D. Complement and PMNL

After incubation, 10 µL of baby rabbit complement (aliquots of fresh collected young rabbit serum and stored at −80° C. before using) and 40 µL of PMNL $2.8\times10^5$ cells was added. The mixture was incubated at 37° C. in a 5% $CO_2$ atmosphere for 60 minutes.

E. CFU Counts

To obtain viable cell counts, a 20 µL aliquot of two dilutions, 1:10 and 1:100 from each sample, was inoculated on triplicate blood agar plates and kept at 37° C. overnight. Complement control included all test reagents except antibodies to pneumococci.

F. Opsonophagocytic Activity

Opsonophagocytic titers are reported as the reciprocal of the highest serum dilution with >50% killing of bacteria compared with growth in the complement control.

As shown in Tables 5 and 6, mice (e.g., mice numbers 1, 2, 3, 4, 5, and 7) with higher antibody responses against serotype 14 polysaccharide and pseudopneumolysin showed higher opsonization activity, whereas mice (e.g., mice numbers 6 and 8) with lower antibody titers against serotype 14 polysaccharide and pseudopneumolysin showed lower opsonization activity. No opsonization activity was detected in mice injected with PBS.

TABLE 5

Opsonization Activity of Mouse Antibody Against Serotype 14 Polysaccharide

| Mouse # Vaccine | Serum dilution | | | | | | | | |
| --- | --- | --- | --- | --- | --- | --- | --- | --- | --- |
| | 1:2 | 1:4 | 1:8 | 1:16 | 1:32 | 1:64 | 1:128 | 1:256 | Control |
| 1, CFU | | 12 | 20 | 22 | 25 | 28 | 32 | 45 | 81 |
| % of killing | | 85% | 76% | 73% | 69% | 65% | 60% | 44% | |
| 2, CFU | | 17 | 18 | 17 | 17 | 32 | 50 | 51 | 81 |
| % of killing | | 79% | 78% | 79% | 79% | 60% | 38% | 37% | |
| 3, CFU | | 19 | 27 | 31 | 31 | 32 | 44 | 56 | 81 |
| % of killing | | 77% | 67% | 62% | 62% | 60% | 46% | 31% | |
| 4, CFU | | 15 | 22 | 23 | 19 | 33 | 36 | 40 | 81 |
| % of killing | | 81% | 73% | 72% | 77% | 59% | 56% | 51% | |
| 5, CFU | | 22 | 26 | 34 | 27 | 33 | 43 | 51 | 81 |
| % of killing | | 73% | 68% | 58% | 67% | 59% | 47% | 37% | |
| 6, CFU | | 22 | 17 | 19 | 28 | 43 | 51 | 57 | 81 |
| % of killing | | 73% | 79% | 77% | 65% | 47% | 37% | 30% | |
| 7, CFU | | 22 | 29 | 29 | 26 | 28 | 29 | 57 | 81 |
| % of killing | | 73% | 64% | 64% | 68% | 65% | 64% | 30% | |
| 8, CFU | | 31 | 23 | 31 | 35 | 48 | 63 | 63 | 81 |
| % of killing | | 62% | 72% | 62% | 57% | 41% | 22% | 22% | |

The titer of mouse serum for opsonization activity
1, 128 #2, 64 #3, 64 #4, 256 #5, 128 #6, 32 #7, 128 #8, 32.

TABLE 6

Antibody (Ab) Responses Against Serotype 14 Polysaccharide (PS) and Pseudopneumolysin (PPN)

| | Ab against PS | | Ab against PPN | |
| --- | --- | --- | --- | --- |
| Mouse# | Titer | $OD_{405}$ (1:300) | Titer | $OD_{405}$ (1:300) |
| 1 | 76800 | 0.735 | 9600 | 0.454 |
| 2 | 76800 | 0.520 | 9600 | 0.360 |
| 3 | 76800 | 0.738 | 9600 | 0.285 |
| 4 | 19200 | 0.677 | 9600 | 0.266 |
| 5 | 19200 | 0.684 | 9600 | 0.381 |
| 6 | 4800 | 0.518 | 4800 | 0.261 |
| 7 | 76800 | 0.815 | 9600 | 0.348 |
| 8 | 4800 | 0.585 | 1200 | 0.125 |

OTHER EMBODIMENTS

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

The invention claimed is:

1. A mammalian expression vector comprising a promoter operably linked to a nucleotide sequence comprising a nucleic acid encoding a polypeptide comprising a fragment of at least 400 contiguous amino acids of a *Streptococcus pneumoniae* pneumolysin protein, wherein the polypeptide lacks the amino acid sequence KVEND (SEQ ID NO:22), wherein the polypeptide lacks hemolytic activity, wherein the *Streptococcus pneumoniae* pneumolysin protein comprises the amino acid of SEQ ID NO: 1, and wherein the polypeptide elicits an immune response against *Streptococcus pneumoniae* when the expression vector is administered to a mammal.

2. The mammalian expression vector of claim 1, wherein the polypeptide comprises amino acids 1-460 of SEQ ID NO:1.

3. The mammalian expression vector of claim 1, wherein the polypeptide comprises amino acids 1-464 of SEQ ID NO:1.

4. The mammalian expression vector of claim 1, wherein the polypeptide comprises amino acids 1-465 of SEQ ID NO:1.

5. The mammalian expression vector of claim 1, wherein the polypeptide comprises amino acids 1-466 of SEQ ID NO:1.

6. The mammalian expression vector of claim 1, wherein the polypeptide comprises amino acids 1-469 of SEQ ID NO:1.

7. The mammalian expression vector of claim 1, wherein the polypeptide comprises amino acids 1-470 of SEQ ID NO:1.

8. The mammalian expression vector of claim 1, wherein the polypeptide lacks the amino acid sequence EDKVEND (SEQ ID NO:23).

9. The mammalian expression vector of claim 1, wherein the polypeptide lacks the amino acid sequence YPQVEDKVEND (SEQ ID NO:24).

10. The expression vector of claim 1, wherein the polypeptide consists of amino acid residues 1-460 of SEQ ID NO:1.

11. The mammalian expression vector of claim 1, wherein the polypeptide consists of amino acid residues 1-464 of SEQ ID NO:1.

12. The mammalian expression vector of claim 1, wherein the polypeptide consists of amino acid residues 1-465 of SEQ ID NO:1.

13. The mammalian expression vector of claim 1, wherein the polypeptide consists of amino acid residues 1-466 of SEQ ID NO:1.

14. The mammalian expression vector of claim 1, wherein the polypeptide consists of amino acid residues 1-469 of SEQ ID NO:1.

15. The mammalian expression vector of claim 1, wherein the polypeptide consists of amino acid residues 1-470 of SEQ ID NO:1.

16. The mammalian expression vector of claim 1, wherein the immune response comprises a humoral immune response.

17. The mammalian expression vector of claim 1, wherein the immune response comprises a cellular immune response.

18. The mammalian expression vector of claim 1, wherein the immune response is directed against a *Streptococcus pneumoniae* pneumolysin protein.

* * * * *

SEQUENCE LISTING

<160> NUMBER OF SEQ ID NOS: 26

<210> SEQ ID NO 1
<211> LENGTH: 471
<212> TYPE: PRT
<213> ORGANISM: Streptococcus pneumoniae

<400> SEQUENCE: 1

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser

-continued

```
                355                 360                 365
Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
    435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470
```

```
<210> SEQ ID NO 2
<211> LENGTH: 38
<212> TYPE: DNA
<213> ORGANISM: Artificial Sequence
<220> FEATURE:
<223> OTHER INFORMATION: primer

<400> SEQUENCE: 2
gactagatct ccatatggca aataaagcag taaatgac                              38

<210> SEQ ID NO 3
<211> LENGTH: 34
<212> TYPE: DNA
<213> ORGANISM: Artificial Sequence
<220> FEATURE:
<223> OTHER INFORMATION: primer

<400> SEQUENCE: 3
cagtggatcc ttactagtca ttttctacct tatc                                  34

<210> SEQ ID NO 4
<211> LENGTH: 38
<212> TYPE: DNA
<213> ORGANISM: Artificial Sequence
<220> FEATURE:
<223> OTHER INFORMATION: primer

<400> SEQUENCE: 4
gactgctagc caccatggca aataaagcag taaatgac                              38

<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5
gactggatcc ttactagaga gttgttcccc aaatag                                36

<210> SEQ ID NO 6
<211> LENGTH: 35
<212> TYPE: DNA
<213> ORGANISM: Artificial Sequence
<220> FEATURE:
<223> OTHER INFORMATION: primer
```

```
<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
gactggatcc ttactattct accttatctt ctacctgag                            39

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
gactggatcc ttactaattt ctaccttat cttctacctg ag                         42

<210> SEQ ID NO 9
<211> LENGTH: 1413
<212> TYPE: DNA
<213> ORGANISM: Artificial Sequence
<220> FEATURE:
<223> OTHER INFORMATION: synthetically generated construct

<400> SEQUENCE: 9
atggcaaata aagcagtaaa tgactttata ctagctatga attacgataa aaagaaactc      60
ttgacccatc agggagaaag tattgaaaat cgtttcatca agagggtaa tcagctaccc     120 gatgagtttg ttgttatcga agaaagaag cggagcttgt cgacaaatac aagtgatatt     180
tctgtaacag ctaccaacga cagtcgcctc tatcctggag cacttctcgt agtggatgag     240
accttgttag agaataatcc cactcttctt gcggtcgatc gtgctccgat gacttatagt     300
attgatttgc ctggtttggc aagtagcgat agctttctcc aagtggaaga ccccagcaat     360
tcaagtgttc gcggagcggt aaacgatttg ttggctaagt ggcatcaaga ttatggtcag     420
gtcaataatg tcccagctag aatgcagtat gaaaaaatca cggctcacag catggaacaa     480
ctcaaggtca agtttggttc tgactttgaa aagacaggga attctcttga tattgatttt     540
aactctgtcc attcaggcga aaagcagatt cagattgtta attttaagca gatttattat     600
acagtcagcg tagatgctgt taaaaatcca ggagatgtgt ttcaagatac tgtaacggta     660
gaggatttaa acagagagg aatttctgca gagcgtcctt tggtctatat ttcgagtgtt     720
gcttatgggc gccaagtcta tctcaagttg gaaaccacga gtaagagtga tgaagtagag     780
gctgcttttg aagctttgat aaaggagtc aaggtagctc ctcagacaga gtggaaacag     840
attttggaca atacagaagt gaaggcggtt attttagggg gcgacccaag ttcgggtgcc     900
cgagttgtaa caggcaaggt ggatatggta gaggacttga ttcaagaagg cagtcgcttt     960
acagcagatc atccaggctt gccgatttcc tatacaactt cttttttacg tgacaatgta    1020
gttgcgacct tcaaaatag tacagactat gttgagacta aggttacagc ttacagaaac    1080
ggagatttac tgctggatca tagtggtgcc tatgttgccc aatattatat tacttggaat    1140
gaattatcct atgatcatca aggtaaggaa gtcttgactc ctaaggcttg ggacagaaat    1200
gggcaggatt taacggctca ctttaccact agtattcctt taaaagggaa tgttcgtaat    1260
```
ctctctgtca aaattagaga gcgttccggg cttgcctggg aatggtggcg tacggtttat   1320
gaaaaaaccg atttgccact agtgcgtaag cggacgattt ctatttgggg aacaactctc   1380
tatcctcagg tagaagataa ggtagaaaat gac                                1413

<210> SEQ ID NO 10
<211> LENGTH: 1380
<212> TYPE: DNA
<213> ORGANISM: Artificial Sequence
<220> FEATURE:
<223> OTHER INFORMATION: synthetically generated construct

<400> SEQUENCE: 10
atggcaaata aagcagtaaa tgactttata ctagctatga attacgataa aaagaaactc     60
ttgacccatc agggagaaag tattgaaaat cgtttcatca agagggtaa tcagctaccc    120 gatgagtttg ttgttatcga agaaagaag cggagcttgt cgacaaatac aagtgatatt    180
tctgtaacag ctaccaacga cagtcgcctc tatcctggag cacttctcgt agtggatgag    240
accttgttag agaataatcc cactcttctt gcggtcgatc gtgctccgat gacttatagt    300
attgatttgc ctggtttggc aagtagcgat agctttctcc aagtggaaga ccccagcaat    360
tcaagtgttc gcggagcggt aaacgatttg ttggctaagt ggcatcaaga ttatggtcag    420
gtcaataatg tcccagctag aatgcagtat gaaaaaatca cggctcacag catggaacaa    480
ctcaaggtca gtttggttc tgactttgaa aagacaggga attctcttga tattgatttt    540
aactctgtcc attcaggcga aaagcagatt cagattgtta atttaagca gatttattat    600 acagtcagcg tagatgctgt taaaaatcca ggagatgtgt tcaagatac tgtaacggta    660 gaggatttaa acagagagg aatttctgca gagcgtcctt tggtctatat ttcgagtgtt    720
gcttatgggc gccaagtcta tctcaagttg gaaaccacga gtaagagtga tgaagtagag    780
gctgcttttg aagctttgat aaaaggagtc aaggtagctc ctcagacaga gtggaaacag    840
attttggaca atacagaagt gaaggcggtt attttagggg gcgacccaag ttcgggtgcc    900
cgagttgtaa caggcaaggt ggatatggta gaggacttga ttcaagaagg cagtcgcttt    960
acagcagatc atccaggctt gccgatttcc tatacaactt cttttttacg tgacaatgta   1020
gttgcgacct ttcaaaatag tacagactat gttgagacta aggttacagc ttacagaaac   1080
ggagatttac tgctggatca tagtggtgcc tatgttgccc aatattatat tacttggaat   1140
gaattatcct atgatcatca aggtaaggaa gtcttgactc ctaaggcttg ggacagaaat   1200
gggcaggatt taacggctca ctttaccact agtattcctt taaaagggaa tgttcgtaat   1260
ctctctgtca aaattagaga gcgttccggg cttgcctggg aatggtggcg tacggtttat   1320
gaaaaaaccg atttgccact agtgcgtaag cggacgattt ctatttgggg aacaactctc   1380

<210> SEQ ID NO 11
<211> LENGTH: 42
<212> TYPE: DNA
<213> ORGANISM: Artificial Sequence
<220> FEATURE:
<223> OTHER INFORMATION: primer

<400> SEQUENCE: 11
gactaagctt gccaccatgg aaattaatgt gagtaaatta ag                         42

<210> SEQ ID NO 12
<211> LENGTH: 34
<212> TYPE: DNA

<213> ORGANISM: Artificial Sequence
<220> FEATURE:
<223> OTHER INFORMATION: primer

<400> SEQUENCE: 12

```
ctgactcgag ttattttact gtaatcaagc catc                                34
```

<210> SEQ ID NO 13
<211> LENGTH: 954
<212> TYPE: DNA
<213> ORGANISM: Artificial Sequence
<220> FEATURE:
<223> OTHER INFORMATION: pSA-59 Aly insert

<400> SEQUENCE: 13

```
atggaaatta atgtgagtaa attaagaaca gatttgcctc aagttggcgt gcaaccatat      60
aggcaagtac acgcacactc aactgggaat ccgcattcaa ccgtacagaa tgaagcggat     120
tatcattggc ggaaagaccc agaattaggt ttttctcgc acattgttgg gaacggatgc     180
atcatgcagg taggacctgt taataatggt gcctgggacg ttggggcgg ttggaatgct     240
gagacctatg cagcggttga actgattgaa agccattcaa ctaaagaaga gttcatgacg     300
gactaccgcc tttatatcga actcttacgc aatctagcag atgaagcagg tttgccgaaa     360
acgcttgata cagggagttt agctggaatt aaaacgcacg agtattgcac gaataaccaa     420
ccaaacaacc actcagacca tgtggatcca taccctact tggcaaaatg gggcattagc     480
cgtgagcagt ttaagcatga tattgagaac ggcttgacga ttgaaacagg ctggcagaag     540
aatgacactg gctactggta cgtacattca gacggctctt atccaaaaga caagtttgag     600
aaaatcaatg gcacttggta ctactttgac agttcaggct atatgcttgc agaccgctgg     660
aggaagcaca cagacggcaa ttggtactac tttgaccaat caggcgaaat ggctacaggc     720
tggaagaaaa tcgctgagaa gtggtactat ttcaacgaag aaggtgccat gaagacaggc     780
tgggtcaagt acaaggacac ttggtactac ttagacgcta agaaggcgc aatggtatca     840
aatgccttta ccagtcagc ggacggaaca ggctggtact acctcaaacc agacggaaca     900
ctggcagaca agccagaatt cacagtagag ccagatggct gattacagt aaaa            954
```

<210> SEQ ID NO 14
<211> LENGTH: 318
<212> TYPE: PRT
<213> ORGANISM: Artificial Sequence
<220> FEATURE:
<223> OTHER INFORMATION: polypeptide of pSA-59 Aly insert sequence

<400> SEQUENCE: 14

```
Met Glu Ile Asn Val Ser Lys Leu Arg Thr Asp Leu Pro Gln Val Gly
  1               5                  10                  15

Val Gln Pro Tyr Arg Gln Val His Ala His Ser Thr Gly Asn Pro His
             20                  25                  30

Ser Thr Val Gln Asn Glu Ala Asp Tyr His Trp Arg Lys Asp Pro Glu
         35                  40                  45

Leu Gly Phe Phe Ser His Ile Val Gly Asn Gly Cys Ile Met Gln Val
     50                  55                  60

Gly Pro Val Asn Asn Gly Ala Trp Asp Val Gly Gly Trp Asn Ala
 65                  70                  75                  80

Glu Thr Tyr Ala Ala Val Glu Leu Ile Glu Ser His Ser Thr Lys Glu
                 85                  90                  95

Glu Phe Met Thr Asp Tyr Arg Leu Tyr Ile Glu Leu Leu Arg Asn Leu
```

```
                    100                 105                 110
Ala Asp Glu Ala Gly Leu Pro Lys Thr Leu Asp Thr Gly Ser Leu Ala
        115                 120                 125

Gly Ile Lys Thr His Glu Tyr Cys Thr Asn Asn Gln Pro Asn Asn His
    130                 135                 140

Ser Asp His Val Asp Pro Tyr Pro Tyr Leu Ala Lys Trp Gly Ile Ser
145                 150                 155                 160

Arg Glu Gln Phe Lys His Asp Ile Glu Asn Gly Leu Thr Ile Glu Thr
                165                 170                 175

Gly Trp Gln Lys Asn Asp Thr Gly Tyr Trp Tyr Val His Ser Asp Gly
            180                 185                 190

Ser Tyr Pro Lys Asp Lys Phe Glu Lys Ile Asn Gly Thr Trp Tyr Tyr
        195                 200                 205

Phe Asp Ser Ser Gly Tyr Met Leu Ala Asp Arg Trp Arg Lys His Thr
    210                 215                 220

Asp Gly Asn Trp Tyr Tyr Phe Asp Gln Ser Gly Glu Met Ala Thr Gly
225                 230                 235                 240

Trp Lys Lys Ile Ala Glu Lys Trp Tyr Tyr Phe Asn Glu Glu Gly Ala
                245                 250                 255

Met Lys Thr Gly Trp Val Lys Tyr Lys Asp Thr Trp Tyr Tyr Leu Asp
            260                 265                 270

Ala Lys Glu Gly Ala Met Val Ser Asn Ala Phe Ile Gln Ser Ala Asp
        275                 280                 285

Gly Thr Gly Trp Tyr Tyr Leu Lys Pro Asp Gly Thr Leu Ala Asp Lys
    290                 295                 300

Pro Glu Phe Thr Val Glu Pro Asp Gly Leu Ile Thr Val Lys
305                 310                 315
```

<210> SEQ ID NO 15
<211> LENGTH: 43
<212> TYPE: DNA
<213> ORGANISM: Artificial Sequence
<220> FEATURE:
<223> OTHER INFORMATION: primer

<400> SEQUENCE: 15
gactaagctt gccaccatgg aagaagctcc cgtagctagt cag                43

<210> SEQ ID NO 16
<211> LENGTH: 37
<212> TYPE: DNA
<213> ORGANISM: Artificial Sequence
<220> FEATURE:
<223> OTHER INFORMATION: primer

<400> SEQUENCE: 16
gactctcgag ctatccatca gggcctaact cattaag                      37

<210> SEQ ID NO 17
<211> LENGTH: 1377
<212> TYPE: DNA
<213> ORGANISM: Artificial Sequence
<220> FEATURE:
<223> OTHER INFORMATION: pSA-60 PspA insert

<400> SEQUENCE: 17
atggaagaag ctcccgtagc tagtcagtct aaagctgaga agactatga tgcagcagtg    60 aaaaaatctg aagctgctaa gaaggcttac gaagaagcta aaaagaaagc agaagacgct   120

```
cagaaaaaat atgatgagga tcagaagaaa actgaggcaa aagcggataa ggaagcaaaa       180
gcatctgcgg aaatagataa agccacgttt gctgtacaaa gtgcgtatgt aaaatttta        240
aatgtccaat ctaatcgtca aatttcggag aatgaacgaa aaaacaatt agcagaaata        300
gataaagaga tagagaatgc taaacaaat ttacagaata acaggaaga atttaataag         360
gttagagcag aagtaattcc tgaagcaaag gggttagctg ttactaaaca aaagcggaa         420
gaagctaaaa aagaagcaga agtagctaag agaaaatatg attatgcaac tctaaaggta       480
gcactagcga agaaagaagt agaggctaag gaacttgaaa ttgaaaaact tcaatatgaa       540
atttctactt tggaacaaga agttgctatt gctcaacatc aagtagataa tttgaaaaaa       600
cttcttgctg gtgcggatcc tgatgatggc acaaaagtta tagaagctaa attaaacaaa       660
ggagaagctg agctaaacgc taaacaagct gagttagcaa aaaacaaac agaacttgaa        720
aaacttcttg acagccttga tcctgaaggt aagactcagg atgaattaga taagaagct         780
gctgaagctg agttggataa aaaagctgat gaacttcaaa ataaagttgc tgatttagaa       840
aaaggaattg ctccttatca aatcaaagtc gctgaattaa ataaagaaat tgctagactt       900
caaagcgatt taaagatgc tgaagaaaat aatgtagaag actatattaa agaaggttta        960
gagcaagcta tcgctgataa aaaagctgaa ttagctacaa ctcaacaaaa catagataaa      1020
actcaaaaag atttagagga tgctgaatta gaacttgaaa agtattagc tacattagac      1080
cctgaaggta aaactcaaga tgaattagat aaagaagctg cagaagatgc taatattgaa      1140
gctcttcaaa acaaagttgc tgatctagaa acaaggttg ctgaattaga taagaagtt         1200
actagacttc aaagcgattt aaaagatgct gaagaaaaca atgtagaaga ctacgttaaa      1260
gaaggcttag ataagctct tactgataaa aaagttgaat taataatac tcaaaaagca        1320
ttagatactg ctcaaaaagc attagatact gctcttaatg agttaggccc tgatgga       1377
```

<210> SEQ ID NO 18
<211> LENGTH: 459
<212> TYPE: PRT
<213> ORGANISM: Artificial Sequence
<220> FEATURE:
<223> OTHER INFORMATION: polypeptide of pSA-60 PspA insert sequence

<400> SEQUENCE: 18

```
Met Glu Glu Ala Pro Val Ala Ser Gln Ser Lys Ala Glu Lys Asp Tyr
 1               5                  10                  15

Asp Ala Ala Val Lys Lys Ser Glu Ala Ala Lys Ala Tyr Glu Glu
            20                  25                  30

Ala Lys Lys Lys Ala Glu Asp Ala Gln Lys Lys Tyr Asp Glu Asp Gln
        35                  40                  45

Lys Lys Thr Glu Ala Lys Ala Asp Lys Glu Ala Lys Ala Ser Ala Glu
    50                  55                  60

Ile Asp Lys Ala Thr Phe Ala Val Gln Ser Ala Tyr Val Lys Phe Leu
65                  70                  75                  80

Asn Val Gln Ser Asn Arg Gln Ile Ser Glu Asn Glu Arg Lys Lys Gln
                85                  90                  95

Leu Ala Glu Ile Asp Lys Glu Ile Glu Asn Ala Lys Gln Asn Leu Gln
            100                 105                 110

Asn Lys Gln Glu Glu Phe Asn Lys Val Arg Ala Glu Val Ile Pro Glu
        115                 120                 125

Ala Lys Gly Leu Ala Val Thr Lys Gln Lys Ala Glu Glu Ala Lys Lys
    130                 135                 140
```

-continued

```
Glu Ala Glu Val Ala Lys Arg Lys Tyr Asp Tyr Ala Thr Leu Lys Val
145                 150                 155                 160

Ala Leu Ala Lys Lys Glu Val Glu Ala Lys Glu Leu Glu Ile Glu Lys
                165                 170                 175

Leu Gln Tyr Glu Ile Ser Thr Leu Glu Gln Val Ala Ile Ala Gln
        180                 185                 190

His Gln Val Asp Asn Leu Lys Lys Leu Leu Ala Gly Ala Asp Pro Asp
        195                 200                 205

Asp Gly Thr Lys Val Ile Glu Ala Lys Leu Asn Lys Gly Glu Ala Glu
        210                 215                 220

Leu Asn Ala Lys Gln Ala Glu Leu Ala Lys Lys Gln Thr Glu Leu Glu
225                 230                 235                 240

Lys Leu Leu Asp Ser Leu Asp Pro Glu Gly Lys Thr Gln Asp Glu Leu
                245                 250                 255

Asp Lys Glu Ala Ala Glu Ala Glu Leu Asp Lys Lys Ala Asp Glu Leu
                260                 265                 270

Gln Asn Lys Val Ala Asp Leu Glu Lys Gly Ile Ala Pro Tyr Gln Ile
            275                 280                 285

Lys Val Ala Glu Leu Asn Lys Glu Ile Ala Arg Leu Gln Ser Asp Leu
    290                 295                 300

Lys Asp Ala Glu Glu Asn Asn Val Glu Asp Tyr Ile Lys Glu Gly Leu
305                 310                 315                 320

Glu Gln Ala Ile Ala Asp Lys Lys Ala Glu Leu Ala Thr Thr Gln Gln
                325                 330                 335

Asn Ile Asp Lys Thr Gln Lys Asp Leu Glu Asp Ala Glu Leu Glu Leu
            340                 345                 350

Glu Lys Val Leu Ala Thr Leu Asp Pro Glu Gly Lys Thr Gln Asp Glu
        355                 360                 365

Leu Asp Lys Glu Ala Ala Glu Asp Ala Asn Ile Glu Ala Leu Gln Asn
        370                 375                 380

Lys Val Ala Asp Leu Glu Asn Lys Val Ala Glu Leu Asp Lys Glu Val
385                 390                 395                 400

Thr Arg Leu Gln Ser Asp Leu Lys Asp Ala Glu Glu Asn Asn Val Glu
                405                 410                 415

Asp Tyr Val Lys Glu Gly Leu Lys Ala Leu Thr Asp Lys Lys Val
            420                 425                 430

Glu Leu Asn Asn Thr Gln Lys Ala Leu Asp Thr Ala Gln Lys Ala Leu
        435                 440                 445

Asp Thr Ala Leu Asn Glu Leu Gly Pro Asp Gly
    450                 455
```

<210> SEQ ID NO 19
<211> LENGTH: 34
<212> TYPE: DNA
<213> ORGANISM: Artificial Sequence
<220> FEATURE:
<223> OTHER INFORMATION: primer

<400> SEQUENCE: 19
ctgaggatcc ttactaagct gtaaccttag tctc        34

<210> SEQ ID NO 20
<211> LENGTH: 37
<212> TYPE: DNA
<213> ORGANISM: Artificial Sequence
<220> FEATURE:
<223> OTHER INFORMATION: primer

```
<400> SEQUENCE: 20
caaaattaga gaacgttccg ggcttgcctg ggaatgg                              37

<210> SEQ ID NO 21
<211> LENGTH: 37
<212> TYPE: DNA
<213> ORGANISM: Artificial Sequence
<220> FEATURE:
<223> OTHER INFORMATION: primer

<400> SEQUENCE: 21
gcccggaacg ttctctaatt ttgacagaga gattacg                              37

<210> SEQ ID NO 22
<211> LENGTH: 5
<212> TYPE: PRT
<213> ORGANISM: Streptococcus pneumoniae

<400> SEQUENCE: 22

Lys Val Glu Asn Asp
 1               5

<210> SEQ ID NO 23
<211> LENGTH: 7
<212> TYPE: PRT
<213> ORGANISM: Streptococcus pneumoniae

<400> SEQUENCE: 23

Glu Asp Lys Val Glu Asn Asp
 1               5

<210> SEQ ID NO 24
<211> LENGTH: 11
<212> TYPE: PRT
<213> ORGANISM: Streptococcus pneumoniae

<400> SEQUENCE: 24

Tyr Pro Gln Val Glu Asp Lys Val Glu Asn Asp
 1               5                  10

<210> SEQ ID NO 25
<211> LENGTH: 39
<212> TYPE: DNA
<213> ORGANISM: Artificial Sequence
<220> FEATURE:
<223> OTHER INFORMATION: primer

<400> SEQUENCE: 25
ctgaggatcc ttactatacc tgaggataga gagttgttc                            39

<210> SEQ ID NO 26
<211> LENGTH: 33
<212> TYPE: DNA
<213> ORGANISM: Artificial Sequence
<220> FEATURE:
<223> OTHER INFORMATION: primer

<400> SEQUENCE: 26
gactggatcc ctatacctga ggatagagag ttg                                  33
```